United States Patent
Herr et al.

(10) Patent No.: US 11,273,060 B2
(45) Date of Patent: *Mar. 15, 2022

(54) ARTIFICIAL ANKLE-FOOT SYSTEM WITH SPRING, VARIABLE-DAMPING, AND SERIES-ELASTIC ACTUATOR COMPONENTS

(71) Applicant: Massachusetts Institute of Technology, Cambridge, MA (US)

(72) Inventors: Hugh M. Herr, Somerville, MA (US); Kwok Wai Samuel Au, Mountain View, CA (US); Daniel Joseph Paluska, Silverthorne, CO (US); Peter Dilworth, Brighton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 275 days.

This patent is subject to a terminal disclaimer.

(21) Appl. No.: 16/458,421

(22) Filed: Jul. 1, 2019

(65) Prior Publication Data
US 2019/0321201 A1    Oct. 24, 2019

Related U.S. Application Data

(60) Division of application No. 15/091,895, filed on Apr. 6, 2016, now Pat. No. 10,342,681, which is a
(Continued)

(51) Int. Cl.
*A61F 2/68* (2006.01)
*A61F 2/70* (2006.01)
(Continued)

(52) U.S. Cl.
CPC .............. *A61F 2/6607* (2013.01); *A61F 2/60* (2013.01); *A61F 2/70* (2013.01); *B25J 19/0008* (2013.01);
(Continued)

(58) Field of Classification Search
CPC .. A61F 2/6607; A61F 2/60; A61F 2/68; A61F 2/70; B62D 57/032; B25J 19/0008
See application file for complete search history.

(56) References Cited

U.S. PATENT DOCUMENTS

| | | | |
|---|---|---|---|
| 2,489,291 A | 11/1949 | Henschke et al. | |
| 2,529,968 A | 11/1950 | Sartin | |

(Continued)

FOREIGN PATENT DOCUMENTS

| | | | |
|---|---|---|---|
| CN | 101061984 A | 10/2007 | |
| CN | 101111211 A | 1/2008 | |

(Continued)

OTHER PUBLICATIONS

Abbas, J.J. et al., "Neural Network Control of Functional Neuromuscular Stimulation Systems: Computer Simulation Studies," *IEEE Transactions on Biomedical Engineering*, vol. 42, No. 11, pp. 1117-1127, Nov. 1995.

(Continued)

*Primary Examiner* — Bruce E Snow
(74) *Attorney, Agent, or Firm* — Hamilton, Brook, Smith & Reynolds, P.C.

(57) ABSTRACT

An artificial foot and ankle joint consists of a curved leaf spring foot member having a heel extremity and a toe extremity, and a flexible elastic ankle member that connects the foot member for rotation at the ankle joint. An actuator motor applies torque to the ankle joint to orient the foot when it is not in contact with the support surface and to store energy in a catapult spring that is released along with the energy stored in the leaf spring to propel the wearer forward. A ribbon clutch prevents the foot member from rotating in one direction beyond a predetermined limit position. A controllable damper is employed to lock the ankle joint or to absorb mechanical energy as needed. The controller and sensing mechanisms control both the actuator motor and the (Continued)

controllable damper at different times during the walking cycle for level walking, stair ascent, and stair descent.

3 Claims, 12 Drawing Sheets

Related U.S. Application Data continuation of application No. 14/283,323, filed on May 21, 2014, now Pat. No. 9,339,397, which is a division of application No. 13/723,743, filed on Dec. 21, 2012, now Pat. No. 8,734,528, which is a continuation of application No. 13/348,570, filed on Jan. 11, 2012, now abandoned, which is a continuation of application No. 11/495,140, filed on Jul. 29, 2006, now abandoned, which is a continuation-in-part of application No. 11/395,448, filed on Mar. 31, 2006, now abandoned.

(60) Provisional application No. 60/704,517, filed on Aug. 1, 2005, provisional application No. 60/666,876, filed on Mar. 31, 2005.

(51) Int. Cl.
| | |
|---|---|
| A61F 2/66 | (2006.01) |
| A61F 2/60 | (2006.01) |
| B25J 19/00 | (2006.01) |
| B62D 57/032 | (2006.01) |
| A61F 2/50 | (2006.01) |
| A61F 2/64 | (2006.01) |
| A61F 2/76 | (2006.01) |

(52) U.S. Cl.
CPC ............ *B62D 57/032* (2013.01); *A61F 2/605* (2013.01); *A61F 2/64* (2013.01); *A61F 2/68* (2013.01); *A61F 2002/503* (2013.01); *A61F 2002/5004* (2013.01); *A61F 2002/5006* (2013.01); *A61F 2002/509* (2013.01); *A61F 2002/5033* (2013.01); *A61F 2002/5073* (2013.01); *A61F 2002/5075* (2013.01); *A61F 2002/5079* (2013.01); *A61F 2002/6657* (2013.01); *A61F 2002/6678* (2013.01); *A61F 2002/6818* (2013.01); *A61F 2002/701* (2013.01); *A61F 2002/704* (2013.01); *A61F 2002/763* (2013.01); *A61F 2002/764* (2013.01); *A61F 2002/7625* (2013.01); *A61F 2002/7635* (2013.01); *A61F 2002/7645* (2013.01)

(56) References Cited

U.S. PATENT DOCUMENTS

| | | |
|---|---|---|
| 3,016,760 A | 1/1962 | Wrighton et al. |
| 3,098,645 A | 7/1963 | Owens |
| 3,207,497 A | 9/1965 | Schoonover |
| 3,449,769 A | 6/1969 | Mizen |
| 3,844,279 A | 10/1974 | Konvalin |
| 3,871,032 A | 3/1975 | Karas |
| 3,916,450 A | 11/1975 | Minor |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |
| 4,672,955 A | 6/1987 | Cooper |
| 4,843,921 A | 7/1989 | Kremer |
| 4,865,376 A | 9/1989 | Leaver et al. |
| 4,872,665 A | 10/1989 | Chareire |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,936,295 A | 6/1990 | Crane |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,294,873 A | 3/1994 | Seraji |
| RE34,661 E | 7/1994 | Grim |
| 5,327,790 A | 7/1994 | Levin et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,865,770 A | 2/1999 | Schectman |
| 5,885,809 A | 3/1999 | Effenberger et al. |
| 5,888,212 A | 3/1999 | Petrofsky et al. |
| 5,888,213 A | 3/1999 | Sears et al. |
| 5,898,948 A | 5/1999 | Kelly et al. |
| 5,910,720 A | 6/1999 | Williamson et al. |
| 5,932,230 A | 8/1999 | DeGrate |
| 5,944,760 A | 8/1999 | Christensen |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,532,400 B1 | 3/2003 | Jacobs |
| 6,585,774 B2 | 7/2003 | Dean, Jr. et al. |
| 6,589,289 B2 | 7/2003 | Ingimarsson |
| 6,592,539 B1 | 7/2003 | Einarsson et al. |
| 6,610,101 B2 | 8/2003 | Herr et al. |

(56) References Cited

U.S. PATENT DOCUMENTS

| | | |
|---|---|---|
| 6,626,952 B2 | 9/2003 | Janusson et al. |
| 6,660,042 B1 | 12/2003 | Curcie et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,942,629 B2 | 9/2005 | Hepburn et al. |
| 6,945,947 B2 | 9/2005 | Ingimundarson et al. |
| 6,966,882 B2 | 11/2005 | Horst |
| 6,969,408 B2 | 11/2005 | Lecomte et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,314,490 B2 | 1/2008 | Bédard et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,485,152 B2 | 2/2009 | Haynes et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,527,253 B2 | 5/2009 | Sugar et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |

(56) References Cited

U.S. PATENT DOCUMENTS

| | | |
|---|---|---|
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| D643,537 S | 8/2011 | Lee |
| 7,992,849 B2 | 8/2011 | Sugar et al. |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| RE42,903 E | 11/2011 | Deffenbaugh et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,075,633 B2 | 12/2011 | Herr et al. |
| 8,202,325 B2 | 6/2012 | Albrecht-Laatsch et al. |
| 8,287,477 B1 | 10/2012 | Herr et al. |
| 8,376,971 B1 | 2/2013 | Herr et al. |
| 8,419,804 B2 | 4/2013 | Herr et al. |
| 8,500,823 B2 | 8/2013 | Herr et al. |
| 8,512,415 B2 | 8/2013 | Herr et al. |
| 8,555,184 B2 | 10/2013 | Herr |
| 8,734,528 B2 | 5/2014 | Herr et al. |
| 8,864,846 B2 | 10/2014 | Herr et al. |
| 8,870,967 B2 | 10/2014 | Herr et al. |
| 9,149,370 B2 | 10/2015 | Herr et al. |
| 9,221,177 B2 | 12/2015 | Herr et al. |
| 9,339,097 B2 | 5/2016 | Herr et al. |
| 9,339,397 B2 | 5/2016 | Herr et al. |
| 9,539,117 B2 | 1/2017 | Herr et al. |
| 9,975,249 B2 | 5/2018 | Herr et al. |
| 10,137,011 B2 | 11/2018 | Herr et al. |
| 10,307,272 B2 | 6/2019 | Herr et al. |
| 10,342,681 B2 | 7/2019 | Herr et al. |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caselnova |
| 2004/0039454 A1 | 2/2004 | Herr et al. |
| 2004/0049290 A1 | 3/2004 | Bedard |
| 2004/0054423 A1 | 3/2004 | Martin |
| 2004/0064195 A1 | 4/2004 | Herr |
| 2004/0088025 A1 | 5/2004 | Gesotti |
| 2004/0181118 A1 | 9/2004 | Kochamba |
| 2004/0181289 A1 | 9/2004 | Bedard et al. |
| 2005/0007834 A1 | 1/2005 | Hidaka |
| 2005/0038525 A1 | 2/2005 | Doddroe et al. |
| 2005/0043614 A1 | 2/2005 | Huizenga et al. |
| 2005/0049652 A1 | 3/2005 | Tong |
| 2005/0059908 A1 | 3/2005 | Bogert |
| 2005/0085948 A1 | 4/2005 | Herr et al. |
| 2005/0155444 A1 | 7/2005 | Otaki et al. |
| 2005/0192677 A1 | 9/2005 | Ragnarsdottir et al. |
| 2005/0209707 A1 | 9/2005 | Phillips et al. |
| 2005/0228515 A1 | 10/2005 | Musallam et al. |
| 2006/0004307 A1 | 1/2006 | Horst |
| 2006/0064047 A1 | 3/2006 | Shimada et al. |
| 2006/0069448 A1 | 3/2006 | Yasui |
| 2006/0094989 A1 | 5/2006 | Scott et al. |
| 2006/0122711 A1 | 6/2006 | Bedard et al. |
| 2006/0213305 A1 | 9/2006 | Sugar et al. |
| 2006/0224246 A1 | 10/2006 | Clausen et al. |
| 2006/0249315 A1 | 11/2006 | Herr et al. |
| 2006/0258967 A1 | 11/2006 | Fujil et al. |
| 2006/0264790 A1 | 11/2006 | Kruijsen et al. |
| 2006/0276728 A1 | 12/2006 | Ashihara et al. |
| 2007/0016329 A1 | 1/2007 | Herr et al. |
| 2007/0032951 A1 | 2/2007 | Tanenhaus et al. |
| 2007/0043449 A1 | 2/2007 | Herr et al. |
| 2007/0050044 A1 | 3/2007 | Haynes et al. |
| 2007/0123997 A1 | 5/2007 | Herr et al. |
| 2007/0129653 A1 | 6/2007 | Sugar et al. |
| 2007/0145930 A1 | 6/2007 | Zaier |
| 2007/0162152 A1 | 7/2007 | Herr et al. |
| 2007/0267791 A1 | 11/2007 | Hollander et al. |
| 2008/0114272 A1 | 5/2008 | Herr et al. |
| 2008/0155444 A1 | 6/2008 | Pannese et al. |
| 2008/0169729 A1 | 7/2008 | Asai |
| 2009/0030530 A1 | 1/2009 | Martin |
| 2009/0204230 A1 | 8/2009 | Kaltenborn et al. |
| 2009/0222105 A1 | 9/2009 | Clausen |
| 2009/0265018 A1 | 10/2009 | Goldfarb et al. |
| 2010/0113988 A1 | 5/2010 | Matsuoka et al. |
| 2010/0185301 A1 | 7/2010 | Hansen et al. |
| 2010/0241242 A1 | 9/2010 | Herr et al. |
| 2010/0256537 A1 | 10/2010 | Menga |
| 2010/0324699 A1 | 12/2010 | Herr et al. |
| 2011/0040216 A1 | 2/2011 | Herr et al. |
| 2011/0224804 A1 | 9/2011 | Clausen et al. |
| 2011/0245931 A1 | 10/2011 | Clausen et al. |
| 2011/0260380 A1 | 10/2011 | Hollander et al. |
| 2011/0264230 A1 | 10/2011 | Herr et al. |
| 2011/0278857 A1 | 11/2011 | Sugar et al. |
| 2012/0136459 A1 | 5/2012 | Herr et al. |
| 2012/0209405 A1 | 8/2012 | Herr et al. |
| 2012/0271433 A1 | 10/2012 | Galea et al. |
| 2013/0110256 A1 | 5/2013 | Herr et al. |
| 2013/0158444 A1 | 6/2013 | Herr et al. |
| 2013/0197318 A1 | 8/2013 | Herr |
| 2013/0310979 A1 | 11/2013 | Herr et al. |
| 2014/0046455 A1 | 2/2014 | Herr et al. |
| 2014/0088729 A1 | 3/2014 | Herr et al. |
| 2014/0257519 A1 | 9/2014 | Herr et al. |
| 2015/0051710 A1 | 2/2015 | Herr et al. |
| 2016/0207201 A1 | 7/2016 | Herr et al. |
| 2016/0228265 A1 | 8/2016 | Herr et al. |
| 2016/0338857 A1 | 11/2016 | Herr et al. |
| 2017/0049587 A1 | 2/2017 | Herr et al. |
| 2019/0175365 A1 | 6/2019 | Herr et al. |

FOREIGN PATENT DOCUMENTS

| | | |
|---|---|---|
| EP | 1169982 | 1/2002 |
| EP | 1393866 | 3/2004 |
| JP | 2008-87143 A | 4/2008 |
| WO | WO 2001/054630 A1 | 8/2001 |
| WO | WO 2003/005934 A2 | 1/2003 |

(56) References Cited

FOREIGN PATENT DOCUMENTS

| WO | WO 2003/03068453 | | 8/2003 |
|---|---|---|---|
| WO | WO 2004/017872 | A1 | 3/2004 |
| WO | WO 2004/019832 | A1 | 3/2004 |
| WO | WO 2010/027968 | A2 | 3/2010 |
| WO | WO 2010/088616 | | 8/2010 |
| WO | WO 2010/088635 | A1 | 8/2010 |

OTHER PUBLICATIONS

Abul-Haj, C.J. et al., "Functional Assessment of Control Systems for Cybernetic Elbow Prostheses—Part II: Application of the Technique," *IEEE Transactions on Biomedical Engineering*, vol. 17, No. 11, pp. 1037-1047, Nov. 1990.

Aeyels, B., et al., "An EMG-Based Finite State Approach for a Microcomputer-Controlled Above-Knee Prosthesis," Engineering in Medicine and Biology Society 1995, pp. 1315-1316 (1997).

Akazawa, K. et al., "Biomimetic EMG-Prosthesis-Hand, 18th Annual International Conference of the IEEE Engineering in Medicine and Biology Society," Amsterdam pp. 535 and 536, 1996.

Aminian, K. et al., "Estimation of Speed and Incline of Walking Using Neural Network," *IEEE Transactions of Instrumentation and Measurement*, 44(3): 743-746 (1995).

Anderson, F.C. et al., "Dynamic Optimization of Human Walking," *Journal of Biomechanical Engineering*, 123: 381-390 (2001).

Andrews, B.J. et al., "Hybrid FES Orthosis Incorporating Closed Loop Control and Sensory Feedback," *J. Biomed. Eng.*, 10: 189-195(1988).

Arakawa, T. et al., "Natural Motion Generation of Biped Locomotion Robot Using Hierarchical Trajectory Generation Method Consisting of GA, EP Layers," Proceedings of the 1997 IEEE International Conference on Robotics and Automation, Albuquerque, NM., pp. 375-379.

Au, et al., "Initial experimental study on dynamic interaction between an amputee and a powered ankle-foot prosthesis." Workshop on Dynamic Walking: Mechanics and Control of Human and Robot Locomotion, May 2006, Ann Arbor, MI, p. 1.

Au, et al., "Powered Ankle-Foot Prosthesis: The Importance of Series and Parallel Motor Elasticity," IEEE Robotics & Automation Magazine, pp. 52-59, Sep. 2008.

Au, S. et al., "Powered Ankle-Foot Prosthesis to Assist Level-Ground and Stair-Descent Gaits." *Neural Networks*, 21: 654-666 (2008).

Au, S.K. et al., "An Ankle-Foot Emulation System for the Study of Human Walking Biomechanics," Proceedings of the 2006 IEEE International Conference on Robotics and Automation, Orlando, FL, May 2006, pp. 2939-2945.

Au, S.K. et al., "An EMG-Position Controlled System for an Active Ankle-Foot Prosthesis: An Initial Experimental Study," Proceedings of the 2005 IEEE 9th International Conference on Rehabilitation Robotics, Chicago, IL., pp. 375-379.

Au, S.K. et al., "Biomechanical Design of a Powered Ankle-Foot Prosthesis," Proceedings of the 2007 IEEE 10th International Conference on Rehabilitation Robotics, Noordwijk, The Netherlands, pp. 298-303, Jun. 12-15, 2007.

Au, S.K. et al., "Powered Ankle-Foot Prosthesis for the Improvement of Amputee Ambulation," paper presented at the Proceedings of the 29th Annual International Conference of the IEEE Eng. Med. Bio. Soc., Cité Internationale, Lyon, France, (Aug. 2007).

Au, S.K. et al., "Powered Ankle-Foot Prosthesis Improves Walking Metabolic Economy," *IEEE Transactions on Robotics*, 25(1): 51-66 (2009).

Barth, D.G. et al., "Gait Analysis and Energy Cost of Below-Knee Amputees Wearing Six Different Prosthetic Feet," *JPO*, 4(2): 63 (1992).

Baten, Chris T.M. et al., "Inertial Sensing in Ambulatory Back Load Estimation," paper presented at the 18th Annual International Conference of the IEEE Engineering in Medicine and Biology Society, Amsterdam, 1996, pp. 497-498.

Bateni, H. et al., "Kinematic and Kinetic Variations of Below-Knee Amputee Gait." *JPO*, 14(1):1-12 (2002).

Blaya, J. et al., "Active Ankle Foot Orthoses (AAFO)," Artificial Intelligence Laboratory, Massachusetts Institute of Technology, Cambridge, MA, pp. 275-277. (no date given).

Blaya, J.A. et al., "Active Ankle Foot Orthoses (AAFO)," Retrieved from: http://www.ai.mit.edu. Artificial Intelligence Laboratory, Massachusetts Institute of Technology, Cambridge, Massachusetts, pp. 251-253 (no date given).

Blaya, J.A. et al., "Adaptive Control of a Variable-Impedance Ankle-Foot Orthosis to Assist Drop Foot Gait," Artificial Intelligence Lab and Harvard-MIT Division Health Sciences and Technology, Boston, MA, 30 pages, no date given.

Blaya, J.A. et al., "Adaptive Control of a Variable-Impedance Ankle-Foot Orthosis to Assist Drop-Foot Gait," IEEE Transactions on Neural Systems and Rehabilitation Engineering, 12(1): 24-31 (2004).

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003), 88 pages.

Blickhan, R., "The Spring-Mass Model for Running and Hopping," *J. Biomechanics*, 22(11 /12): 1217-1227 (1989).

Bortz, J.E. "A New Mathematical Formulation for Strapdown Inertial Navigation," *IEEE Transactions on Aerospace and Electronic Systems*, AES-7(1): 61-66 (1971).

Bouten, C.V. et al., "Assessment of Energy Expenditure for Physical Activity Using a Triaxial Accelerometer," *Medicine and Science in Sports and Exercise*, 26(12):1516-1523 (1994).

Brockway, J.M., "Derivation of Formulae Used to Calculate Energy Expenditure in Man," *Human Nutrition: Clinical Nutrition* 41C, pp. 463-471 (1987).

Brown, T.G., "On the Nature of the Fundamental Activity of the Nervous Centres; Together with an Analysis of the Conditioning of Rhythmic Activity in Progression, and a Theory of the Evolution of Function in the Nervous System," pp. 24-46 (no date given).

Chu, A. et al., "On the Biomimetic Design of the Berkeley Lower Extremity Exoskeleton," paper presented at the Proceedings of the 2005 IEEE International Conference on Robotics and Automation, Barcelona, Spain, (Apr. 2005) pp. 4556-4363.

Colborne, G.R., et al., "Analysis of mechanical and metabolic factors in the gait of congenital below knee amputees," *Am. J. Phys. Med. Rehabil.*, vol. 92, pp. 272-278, Oct. 1992.

Colgate, J.E., "The Control of Dynamically Interacting Systems," Massachusetts Institute of Technology, pp. 1-15, Aug. 1988.

Collins, S.H. et al., "Controlled Energy Storage and Return Prosthesis Reduces Metabolic Cost of Walking," ISB XXth Congress—ASB 29th Annual Meeting, Jul. 31-Aug. 5, Cleveland, Ohio, pp. 804 (no year given).

Collins, S.H., et al., "A Bipedal Walking Robot with Efficient and Human-Like Gait," 2005 IEEE, Int'l Conference on Robotics and Automation, Barcelona, Spain, pp. 1983-1988, (Apr. 2005).

Collins, S.H., et al., Supporting Online Material for "Efficient Bipedal Robots Based on Passive-Dynamic Walkers," Mechanical Engineering, University of Michigan, Feb. 11, 2005, Ann Arbor, MI, pp. 1-8.

Crago, P.E. et al., "New Control Strategics for Neuroprosthetic Systems," *Journal of Rehabilitation Research and Development*, vol. 33, No. 2, Apr. 1996, pp. 158-172.

Daley, M.A. et al., "Running Stability is Enhanced by a Proximo-Distal Gradient in Joint Neuromechanical Control," *The Journal of Experimental Biology*, vol. 210, pp. 383-394 (Feb. 2007).

Dapena, J. et al., "A Three-Dimensional Analysis of Angular Momentum in the Hammer Throw," Biomechanics Laboratory, Indiana University, IN, *Medicine and Science in Sports and Exercise*, vol. 21, No. 2, pp. 206-220 (1988).

Davids, J.R., "Book Reviews" *Journal of Pediatric Orthopedics* 12, pp. 815, 1992.

Dietz, V. "Proprioccption and Locomotor Disorders," *Nature Reviews*, vol. 3, pp. 781-790 (Oct. 2002).

Dietz, V. "Spinal Cord Pattern Generators for Locomotion," *Clinical Neurophysiology*, vol. 114, Issue 8, pp. 1-12 (Aug. 2003).

(56) References Cited

OTHER PUBLICATIONS

Doerschuk, P.C. et al., "Upper Extremity Limb Function Discrimination Using EMG Signal Analysis," *IEEE Transactions on Biomedical Engineering*, vol. BME-30. No. 1, Jan. 1983, pp. 18-28.

Doke, J. et al., "Mechanics and Energetics of Swinging the Human Leg," *The Journal of Experimental Biology*, vol. 208, pp. 439-445 (2005).

Dollar, A.M. et al., "Lower Extremity Exoskeletons and Active Orthoses: Challenges and State-of-the-Art," *IEEE Transactions on Robotics*, vol. 24, No. 1, pp. 1-15, Feb. 2008.

Donelan, J.M. et al., "Force Regulation of Ankle Extensor Muscle Activity in Freely Walking Cats," *Journal of Neurophysiology*, vol. 101, pp. 360-371 (2009).

Donelan, J.M. et al., "Mechanical work for Step-to-Step Transitions is a Major Determinant of the Metabolic Cost of Human Walking," *The Journal of Experimental Biology*, vol. 205, pp. 3717-3727 (2002).

Donelan, J.M. et al., "Simultaneous Positive and Negative External Mechanical Work in Human Walking," *Journal of Biomechanics*, vol. 35, 2002, pp. 117-124 (2002).

Drake, C., "Foot & Ankle Splints or Orthoses," HemiHelp Information Sheet, London, United Kingdom, 3 pages, http://www.hemihelp.org.uk/leaflets/hbleaflets90.htm Retrieved on: Jun. 20, 2003.

Drake, C., "Ankle & Foot Splints or Orthoses (AFOs)." HemiHelp Information Sheet, pp. 1-6, last revision Dec. 2011.

Drake, C., "Foot & Ankle Splints or Orthoses," HemiHelp Information Sheet No. 13, pp. 1-5, last update Jun. 2009.

Eilenberg, et al., "Control of a Powered Ankle-Foot Prosthesis Based on a Neuromuscular Model, *IEEE Transactions on Neural Systems & Rehabilitation Eng.*", vol. 18(2):164-173 (2010).

Eilenberg, M.F. "A Neuromuscular-Model Based Control Strategy for Powered Ankle-Foot Prostheses," Massachusetts Institute of Technology, pp. 1-90. Jul. 20, 2010.

Ekeberg, Ö et al., "Computer Simulation of Stepping in the Hind Legs of the Cat: An Examination of Mechanisms Regulating the Stance-to-Swing Transition," *J. Neurophysical*, vol. 94, pp. 4256-4268 (2005).

Ekeberg, Ö et al., "Simulations of Neuromuscular Control in Lamprey Swimming," The Royal Society, *Phil. Trans. R. Soc. Land*, vol. 354, pp. 895-902 (1999).

Endo, K. et al., "A Quasi-Passive Model of Human Leg Function in Level-Ground Walking." Proceedings of the 2006 IEEE/RSJ International Conference on Intelligent Robots and Systems, Oct. 9-15, 2006, Beijing, China, pp. 4935-4939.

Eppinger, S.D. et al., "Three Dynamic Problems in Robot Force Control," *IEEE Transactions on Robotics and Automation*, vol. 8, No. 6, pp. 772-778 (Dec. 1992).

Esquenazi, M.D., A., et al., "Rehabilitation After Amputation," *J Am Podiatr Med Assoc* vol. 91, No. 1, pp. 13-22 (Jan. 2001).

Farley, C.T. et al., "Energetics of Walking and Running: Insights From Simulated Reduced-Gravity Experiments," *J. Appl. Physiol.* 73(6):2709-2712 (1992).

Farry, K.A. et al., "Myoelectric Teleoperation of a Complex Robotic Hand," *IEEE Transactions on Robotics and Automation*, vol. 12, No. 5, pp. 775-778 (Oct. 1996).

Featherstone, R., "Robot Dynamics Algorithms." Edinburgh University, pp. 1-173, 1987.

Fite, K. et al., "Design and Control of an Electrically Powered Knee Prosthesis," Proceedings of the 2007 IEEE 10th International Conference on Rehabilitation Robotics, June 12-15, The Netherlands, pp. 902-905.

Flowers. W.C., "A Man-Interactive Simulator System for Above-Knee Prosthetics Studies," Partial fulfillment for Doctor of Philosophy, MIT, pp. 1-94 Aug. 1972.

Fod, A. et al., "Automated Derivation of Primitives for Movement Classification," *Autonomous Robots*, vol. 12, No. 1, pp. 39-54 (Jan. 2002).

Frigon, A. et al., "Experiments and Models of Sensorimotor Interactions During Locomotion," *Biological Cybernetics*, vol. 95, pp. 606-627 (2006).

Fujita et al., "Joint Angle Control with Command Filter for Human Ankle Movement Using Functional Electrical Stimulation," Proceedings of the Ninth Annual Conference of the IEEE Engineering in Medicine and Biology Society, Boston, MA, Nov. 13-16, 1987.

Fukuda, O. et al., "A Human-Assisting Manipulator Teleoperated by EMG Signals and Arm Motions," *IEEE Transactions on Robotics and Automation*, vol. 19, No. 2, pp. 210-222 (Apr. 2003).

Gates, D.H. Thesis: "Characterizing Ankle Function During Stair Ascent, Descent, and Level Walking for Ankle Prosthesis and Orthosis Design," Boston University, pp. 1-84 (2004).

Gerritsen, K.G.M. et al., "Direct Dynamics Simulation of the Impact Phase in Heel-Toe Running," *J. Biomechanics*, vol. 28, No. 6, pp. 661-668 (1995).

Geyer. H. et al., "A Muscle-Reflex Model That Encodes Principles of Legged Mechanics Predicts Human Walking Dynamics and Muscle Activities," *IEEE Transactions on Neural Systems and Rehabilitation Engineering*, vol. 18, No. 3, pp. 263-273 (Jun. 2010).

Geyer, H. et al., "A Muscle-Reflex Model that Encodes Principles of Legged Mechanics Produces Human Walking Dynamics and Muscle Activities," IEEE Transactions on Neural Systems and Rehabilitation Engineenng, vol. X, No. X, pp. 1-10 (2010).

Geyer, H. et al., "Compliant Leg Behavior Explains Basic Dynamics of Walking and Running," *Proc. R. Soc. B*, vol. 273, pp. 2861-2867 (2006).

Geyer, H. et al., "Positive Force Feedback in Bouncing Gaits?," *Proc. R. Soc. Lond*, B, vol. 270, pp. 2173-2183 (2003).

Ghigliazza, R.M. et al., "A Simply Stabilized Running Model," University of Pennsylvania, *SIAM Journal on Applied Dynamical Systems*, vol. 2, Issue 2, pp. 187-218 (May 8, 2004).

Giszter, S., et al., "Convergent Force Fields Organized in the Frog's Spinal Cord," *Journal of Neuroscience*, 13(2): 467-491 (1993).

Godha, S. et al., "Integrated GPS/INS System for Pedestrian Navigation in a Signal Degraded Environment," ION GNSS, Fort Worth, TX, Sep. 26-29, 2006 pp. 1-14.

Goswami, A. et al., "Rate of Change of Angular Momentum and Balance Maintenance of Biped Robots," Proceedings of the 2004 IEEE International Conference on Robotics and Automation, New Orleans, LA, Apr. 2004, pp. 3785-3790.

Goswami, A., "Postural Stability of Biped Robots and the Foot-Rotation Indicator (FRI) Point," *The International Journal of Robotics Research*, vol. 18, No. 6, pp. 523-533 (Jun. 1999).

Graupe, D. et al., "A Microprocessor System for Multifunctional Control of Upper-Limb Prostheses via Myoelectric Signal Identification," *IEEE Transactions on Automatic Control*, vol. 23, No. 4, pp. 538-544 (Aug. 1978).

Gregoire, L. et al., "Role of Mono- and Biarticular Muscles in Explosive Movements," *International Journal of Sports Medicine*, vol. 5, No. 6, pp. 299-352 (Dec. 1984).

Grillner, S. and Zangger, P., "On the Central Generation of Locomotion in the Low Spinal Cat," *Experimental Brain Research*, 34: 241-261 (1979).

Grimes, D.L., "An Active Multi-Mode Above-Knee Prosthesis Controller," unpublished doctoral dissertation, Massachusetts Institute of Technology (1979).

Gu, W.J., "The Regulation of Angular Momentum During Human Walking," unpublished doctoral dissertation, Massachusetts Institute of Technology, 42 pages (2003).

Gunther, M. et al., "Human Leg Design: Optimal Axial Alignment Under Constraints," *J. Math. Biol.*, 48: 623-646 (2004).

Günther, M., and Ruder, H., "Synthesis of Two-Dimensional Human Walking: a test of the λ-model," *Biol. Cybern.*, 89: 89-106 (2003).

Hanafusa, H. et al., "A Robot Hand with Elastic Fingers and Its Application to Assembly Process," pp. 337-359, Robot Motion, Brady, et al., MIT Press, Cambridge, MA 1982.

Hansen, A.H., et al., "The Human Ankle During Walking: Implications for Design of Biomimetic Ankle Prostheses." *Journal of Biomechanics*, 37: 1467-1474 (2004).

Hayes, W.C., et al., "Leg Motion Analysis During Gait by Multiaxial Accelerometry: Theoretical Foundations and Preliminary Validations. *Journal of Biomechanical Engineering*," 105: 283-289 (1983).

(56) References Cited

OTHER PUBLICATIONS

Heglund, N. et al., "A Simple Design for a Force-Plate to Measure Ground Reaction Forces." *J. Exp. Biol.*, 93: 333-338 (1981).
Herr, H.M. et al., "A Model of Scale Effects in mammalian Quadrupedal Running," *The Journal of Experimental Biology*, 205: 959-967 (2002).
Herr, H.M., and McMahon, T.A., "A Trotting Horse Model," *The International Journal of Robotics Research*, 19: 566-581 (2000).
Herr, H.M., and Popovic, M., "Angular Momentum in Human Walking." *The Journal of Experimental Biology*, 211: 467-481 (2008).
Herr, H.M., and Wilkenfeld, A., "User-adaptive Control of A Magnetorheological Prosthetic Knee," *Industrial Robot: An International Journal*, 30(1): 42-55 (2003).
Herr, Hugh et al. "New Horizons for Orthotic and Prosthetic Technology: Artificial Muscle for Ambulation," The MIT Media Laboratory, pp. 1-9, 2004.
Heyn, A., et al., "The Kinematics of the Swing Phase Obtained From Accelerometer and Gyroscope Measurements," paper presented at the $18^{th}$ Annual International Conference of the IEEE Engineering in Medicine and Biology Society, Amsterdam (1996).
Hill, A.V., "The Heat of Shortening and the Dynamic Constants of Muscle," *Proc. R. Soc. Lond.*, 126: 136-195 (1938).
Hirai, K., et al., "The Development of Honda Humanoid Robot," paper presented at the IEEE International Conference on Robotics & Automation, Leuven, Belgium (1998).
Hitt, J.K., et al., "The Sparky (Spring Ankle with Regenerative Kinetics) Project: Design and Analysis of a Robotic Transtibial Prosthesis with Regenerative Kinetics," Proceedings of the ASME International Design Engineering Technical Conferences and Computers and Information in Engineering Conference, vol. 5 Part C, DETC2007-34512, pp. 1587-1596, Las Vegas, Nevada (Sep. 2007).
Hof, A.L., et al., "Calf Muscle Moment, Work and Efficiency in Level Walking: Role of Series Elasticity," *J Biochem.*, 16: 523-537 (1983).
Hofbaur, M.W., and Williams, B.C., "Mode Estimation of Probabilistic Hybrid Systems," MIT Space Systems and Artificial Intelligence Laboratories and Graz University of Technology, Department of Automatic Control, (No Date given).
Hofbaur, M.W., et al., "Hybrid Diagnosis with Unknown Behavioral Modes," Proceedings of the $13^{th}$ International Workshop on Principles of Diagnosis (DX02) (2002).
Hofmann, A., et al., "A Sliding Controller for Bipedal Balancing Using Integrated Movement of Contact and Non-Contact Limbs," Proceedings of the 2004 IEEE/RSJ International Conference on Intelligence Robots and Systems, Japan (2004).
Hofmann, A.G., "Robust Execution of Bipedal Walking Tasks From Biomechanical Principles," unpublished doctoral dissertation for Massachusetts Institute of Technology (2006).
Hogan, N., "Impedance Control: An Approach to Manipulation," Dept. of Mechanical Engineering and Labortory of Manufacturing and Productivity, Massachusetts Institute of Technology, Cambridge MA, pp. 304-313 (Jun. 1984).
Hogan, N., "Impedance Control: An Approach to Manipulation: Part II—Implementation," *Journal of Dynamic Systems, Measurement, and Control*, 107: 8-16 (1985).
Hogan, N., "A Review of the Methods of Processing EMG for Use As A Proportional Control Signal," *Biomedical Engineering*, 11(3): 81-86 (1976).
Hogan, N., "Impedance Control: An Approach to Manipulation: Part I—Theory," *Journal of Dynamic Systems, Measurement, and Control*, 107: 1-7 (1985).
Hogan, N., "Impedance Control: An Approach to Manipulation: Part III—Application," *Journal of Dynamics Systems, Measurement and Control*, 107: 17-24 (1985).
Hogan, N., and Buerger, S.P., "Impedance and Interaction Control, Robots and Automation Handbook, Chapter 19, © 2005 by CRC Press LLC, 24 pgs."
Holgate, M.A., et al., "The SPARKy (Spring Ankle with Regenerative Kinetics) Project: Choosing a DC Motor Based Actuation Method," Proceedings of the 2nd Biennial IEEE-EMBS International Conf. on Biomedical Robotics and Biomechatronics, Scottsdale, AZ, pp. 163-168, Oct. 19-22, 2008.
Hollander, K.W. et al., "Adjustable Robotic Tendon using a 'Jack Spring'™," Proceedings of the 2005 IEEE, $9^{th}$ International Conference on Rehabilitation Robotics, Jun. 28-Jul. 1, 2005, Chicago, IL, USA, pp. 113-118.
Howard. R.D., Thesis: "Joint and Actuator Design for Enhanced Stability in Robotic Force Control," Submitted to the Dept. of Aeronautics and Astronautics on Aug. 8, 1990 in partial fulfillment of the requirements for the degree of Doctor of Philosophy.
Huang, H.-P. et al., "Development of a Myoelectric Discrimination System for a Multi-Degree Prosthetic Hand," Proceedings of the 1999 IEEE, International Conference on Robotics & Automation, Detroit, Michigan, (1999).
Huang, Q. et al., "Planning Walking Patterns for a Biped Robot," *IEEE Transactions on Robotics and Automation*, 17(3): 280-289 (Jun. 2001).
Hultborn, H., "Spinal reflexes, mechanisms and concepts: From Eccles to Lundberg and beyond," *Progress in Neurobiology*, 78: 215-232 (2006).
Ijspeert, A.J. et al., "From swimming to walking with a salamander robot driven by a spinal cord model," pp. 1-5 (no further info).
Ijspeert, A.J., "Central pattern generators for locomotion control in animals and robots: a review." *Preprint of Neural Networks*, vol. 21, No. 4, pp. 642-653 (2008).
International Preliminary Report on Patentability for International Application No. PCT/US2010/047279; dated Mar. 15, 2012.
International Search Report and Written Opinion for International Application No. PCT/US2009/055600, dated Apr. 29, 2010.
International Search Report and Written Opinion for International Application No. PCT/US2010/047279; dated Jan. 19, 2011.
International Search Report and Written Opinion for International Application No. PCT/US2011/031105, dated Oct. 11, 2011.
International Search Report for PCT/US2010/022783, "Model-Based Neuromechanical Controller for a Robotic Leg", dated May 4, 2010.
Ivashko, D.G. et al., "Modeling the spinal cord neural circuitry controlling cat hindlimb movement during locomotion," *Neurocomputing*, 52-54, pp. 621-629 (2003).
Johansson, J.L. el al., "A Clinical Comparison of Variable-Damping and Mechanically Passive Prosthetic Knee Devices," Variable-Damping vs. Mechanically Passive Prosthetic Knees, *Am J Phys Med Rehabil* 84(8):1-13, (Aug. 2005).
Johnson, C.T. et al., "Experimental Identification of Friction and Its Compensation in Precise, Position Controlled Mechanisms," *IEEE Transactions on Industry Applications*, vol. 28, No. 6, pp. 1392-1398 (Nov./Dec. 1992).
Jonic, S. et al., "Three Machine Learning Techniques for Automatic Determination of Rules to Control Locomotion," *IEEE Transactions on Biomediccd Engineering*, vol. 46, No. 3, pp. 300-310 (Mar. 1999).
Kadaba, M.P. et al., "Measurement of Lower Extremity Kinematics During Level Walking," *Journal of Orthapedic Research*, pp. 383-392, 1990.
Kadaba, M.P. et al., "Repeatability of Kinematic, Kinetic, and Electromyographic Data in Normal Adult Gait," *Journal of Orthopedic Research*, pp. 849-860, 1989.
Kajita, S. et al., "A Hop towards Running Humanoid Biped," Proceedings of the 2004 IEEE International Conference on Robotics & Automation, pp. 629-635, 2004.
Kajita, S. et al., "Biped Walking on a Low Friction Floor," Proceedings of the 2004 IEEE/RSJ International Conference on Intelligent Robots & Systems, pp. 3546-3552, Sep. 28-Oct. 2, 2004, Sendai, Japan.
Kajita, S. et al., "Resolved Momentum Control: Humanoid Motion Planning based on the Linear and Angular Momentum," Proceedings of the 2003 IEEE/RSJ International Conference on Intelligent Robots & Systems, pp. 1644-1650 (2003).
Kaneko, K. et al., "Humanoid Robot HRP-2," Proceedings of the 2004 IEEE International Conference on Robotics & Automation, pp. 1083-1090 (Apr. 2004).

(56) References Cited

OTHER PUBLICATIONS

Kapti, A.O. et al., "Design and control of an active artificial knee joint," *Mechanism and Machine Theory*, vol. 41, pp. 1477-1485 (2006).
Katie, D. et al., "Survey of Intelligent Control Techniques for Humanoid Robots," *Journal of Intelligent and Robotic Systems*, vol. 37, pp. 117-141 (2003).
Kerrigan, D.C. et al., "A refined view of the determinants of gait: Significance of heel," *Archives of Physical Medicine and Rehabilitation*, vol. 81, Issue 8, pp. 1077-1080 (Aug. 2000).
Kerrigan, D.C. et al., "Quantification of pelvic rotation as a determinant of gait," Archives of Physical Medicine and Rehabilitation, vol. 82, Issue 2, pp. 217-220 (Feb. 2001).
Khatib, O. et al., "Coordination and Decentralized Cooperation of Multiple Mobile Manipulators," *Journal of Robotic Systems*, 13(11): 755-764 (1996).
Khatib, O. et al., "Whole-Body Dynamic Behavior And Control Of Human-Like Robots," *International Journal of Humanoid Robotics*, vol. 1, No. 1, pp. 29-43 (2004).
Kidder, S.M. et al., "A System for the Analysis of Foot and Ankle Kinematics During Gait," *IEEE Transactions on Rehabilitation Engineering*, vol. 4, No. 1, pp. 25-32 (Mar. 1996).
Kim, J.-H. et al., "Realization of Dynamic Walking for the Humaniod Robot Platform KHR-1," *Advanced Robotics*, 18(7): 749-768, (2004).
Kirkwood, C.A. et al., "Automatic detection of gait events: a case study using inductive learning techniques," *J. Biomed. Eng.*, vol. 11, pp. 511-516 (Nov. 1989).
Kitayama, I. et al., "A Microcomputer Controlled Intelligent A/K Prosthesis—Fundamental Development," Proceedings, Seventh World Congress of ISPO, Jun. 28-Jul. 3, 1992, Chicago, Illinois, USA, 25 pages.
Klute, G.K. et al., "Intelligent transtibial prostheses with muscle-like actuators." 2002 American Physiological Society Intersociety Meeting: The Power of Comparative Physiology: Evolution, Integration, and Applied, 1 page abstract.
Klute, G.K. et al., "Artificial Muscles: Actuators for Biorobotic Systems," *The International Journal of Robotics Research*, 21(4): 295-309 (2002).
Klute, G.K. et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.
Klute, G.K. et al., "Lower Limb Prostheses Powered by Muscle-Like Pneumatic Actuator," Submitted to Olcodinamica c Pneumatica, Publishe Tecniche Nuovc, Milamo, Italy, Mar. 15, 2000, 6 pages.
Klute, G.K. et al., "McKibben Artificial Muscles: Pneumatic Actuators with Biomechanical Intelligence," IEEE/ASME 1999 International Conference on Advanced Intelligent Mechatronics, Atlanta, GA, pp. 221-226 (Sep. 1999).
Klute, G.K. et al., "Muscle-Like Pneumatic Actuators for Below-Knee Prostheses," Actuator 2000: 7th International Conference on New Actuators, Bremen, Germany on Jun. 9-21, 2000, pp. 289-292.
Klute, G.K. et al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., p. 52 (Oct. 1998).
Klute, G.K. et al., "Variable Stiffness Prosthesis for Transtibial Amputees," Dept of Veteran Affairs, Seattle, WA USA, 2 pages (2003).
Klute, G.K. et al., "Artificial Muscles: Actuators For Lower Limb Prostheses," Abstract in: Proceedings of the $2^{nd}$ Annual Meeting of the VA Rehabilitation Research and Development Service, Washington, D.C., Feb. 20-22, 2000, p. 107.
Klute, G.K. et al., "Mechanical properties of prosthetic limbs: Adapting to the patient, " *Journal of Rehabilitation Research and Development*, vol. 38, No. 3, pp. 299-307 (May/Jun. 2001).
Koganezawa, K. et al., *Biomedical Engineering 1987*, 2.3: Control Aspects of Artificial Leg, pp. 71-85 (1987).

Kondak, K. et al., "Control and Online Computation of Stable Movement for Biped Robots," Proceedings of the 2003 IEEE/RSJ, Int'l Conference on Intelligent Robots and Systems, Las Vegas, Nevada, Oct. 2003, pp. 874-879.
Kostov, A. et al., "Machine Learning in Control of Functional Electrical Stimulation Systems for Locomotion," *IEEE Transactions on Biomedical Engineering*, vol. 42, No. 6, pp. 541-551 (Jun. 1995).
Kuo, A.D., "A Simple Model of Bipedal Walking Predicts the Preferred Speed-Step Length Relationship," *Transactions of the ASME*, vol. 123, pp. 264-269 (Jun. 2001).
Kuo, A.D., "Energetics of Actively Powered Locomotion Using the Simplest Walking Model," *Journal of Biomechanical Engineering*, vol. 124, pp. 113-120 (Feb. 2002).
Lafortune, M.A., "Three-Dimensional Acceleration of the Tibia During Walking and Running," *J. Biomechanics*, vol. 24, No. 10, pp. 877-886 (1991).
LeBlanc, M.K. et al., "Generation and Transfer of Angular Momentum in the Javelin Throw," American Society of Biomechanics, Presented at the $20^{th}$ Annual Meeting of the American Society of Biomechanics, Atlanta, Georgia, Oct. 17-19, 1996, 4 pages.
Li, C. et al., "Research and Development of the Intelligently-Controlled Prosthetic Ankle Joint," Proceedings of the 2006 IEEE International Conference on Mechatronics and Automation, Jun. 25-28, 2006, Luoyana, China, pp. 1114-1119.
Light, L.H. et al., "Skeletal Transients on Heel Strike in Normal Walking with Different Footwear," *J. Biomechanics*, vol. 13, pp. 477-480 (1980).
Liu, X. et al., "Development of a Lower Extremity Exoskeleton for Human Performance Enhancement," Proceedings of 2004 IEEE/RSJ International Conference on Intelligent Robots and Systems, Sep. 28-Oct. 2, 2004, Sendai, Japan, 3889-3894.
Lloyd, R. et al., "Kinetic changes associated with load carriage using two rucksack designs," *Ergonomics*, vol. 43, No. 9, pp. 1331-1341 (2000).
Luinge, H.J., *Inertial Sensing of Human Movement*, Twente University Press, Enschede, the Netherlands, 80 pages (Feb. 15, 1973).
Lundberg, A., "Reflex control of stepping," The Norwegian Academy of Science and Letters, The Nansen Memorial Lecture, Oct. 10, 1968, 40 pages.
Macfarlane, P.A. et al., "Gait Comparisons for Below-Knee Amputees Using a Flex-Foot(TM) Versus a Conventional Prosthetic Foot," JPO 1991, vol. 3, No. 4, pp. 150, htt://www.oandp.org/jpo/library/printArticle.asp?printArticleId=1991_04_150, Retrieved on: Feb. 9, 2012, 10 pages.
Maganaris, C.N., "Force-length characteristics of in vivo human skeletal muscle," *Acta Physiol Scand*, 172: 279-285 (2001).
Maganaris, C.N., "Force-Length Characteristics of the In Vivo Human Gastrocnemius Muscle," *Clinical Anatomy*, 16: 215-223 (2003).
Martens, W.L.J., "Exploring the Information Content and Some Applications of Body Mounted Piezo-Resistive Accelerometers," PhyVision b.v., Gemert, The Netherlands, pp. 9-12, no date given.
Maufroy, C. et al., "Towards a general neural controller for quadrupedal locomotion," *Neural Networks*, 21: 667-681 (2008).
Mayagoitia, R.E. et al., "Accelerometer and rate gyroscope measurement of kinematics: an inexpensive alternative to optical motion analysis systems," *Journal of Biomechanics*, 35: 537-542 (2002).
McFadyen, B.J. et al., "An Integrated Biomechanical Analysis of Normal Stair Ascent and Descent," *J. Biomechanics*, vol. 21, No. 9, pp. 733-744 (1988).
McGeer, T., "Passive Dynamic Walking," The International Journal of Robotics Research, 9, pp. 62-88 (1990).
McGeer, T., Chapter 4: "Principles of Walking and Running." *Advances in Comparative and Environmental Physiology*, Chapter 4, pp. 113-139 (1992).
McIntosh, A.S. et al., "Gait dynamics on an inclined walkway," *J. Biomechanics*, vol. 39, Issue 13, pp. 2491-2502 (2006).
McMahon, T.A. et al., "Groucho Running," *J Appl. Physiol.* 62(6) pp. 2326-2337 (1987).
McMahon, T.A. et al., "The Mechanics of Running: How Does Stiffness Couple with Speed?" *J. Biomechanics*, vol. 23, Suppl. 1, pp. 65-78 (1990).

(56) References Cited

OTHER PUBLICATIONS

Minassian, K. et al., "Human lumbar cord circuitries can be activated by extrinsic tonic input to generate locomotor-like activity," *Human Movement Science*, 26: 275-295 (2007).
Mochon, S. et al., "Ballistic Walking," *J. Biomechanics*, vol. 13, pp. 49-57 (1980).
Molen, N.H., "Energy/Speed Relation of Below-Knee Amputees Walking on a Motor-Driven Treadmill." *Physiol*, 31: 173-185 (1973).
Morris, J.R.W., "Accelerometry—A Technique for the Measurement of Human Body Movements," *J. Biomechanics*, vol. 6, pp. 729-736 (1973).
Muraoka, T. et al., "Muscle fiber and tendon length changes in the human vastus lateralis during show pedaling." *J. Appl. Physiol.*, 91: 2035-2040 (2001).
Nakagawa, A., "Intelligent Knee Mechanism and the Possibility to Apply the Principle to the Other Joints," paper presented at the Proceedings of the 20$^{th}$ Annual International Conference of the IEEE Engineering in Medicine and Biology Society, 20(5): 2282-2287 (1998).
Neal, R. M. et al., "A View of the EM Algorithm That Justifies Incremental, Sparse, and Other Variants," pp. 1-14, no date given.
Ng, S.K. et al., "Fuzzy Model Identification For Classification of Gait Events in Paraplegics," IEEE Transactions on Fuzzy Systems, 5(4) (1997).
Nielsen, D.H. et al., "Comparison of Energy Cost and Gait Efficiency during Ambulation in Below-Knee Ampuees Using Different Prosthetic Feet," JPO, 1:24-31, http://www.oandp.org/jpo/library/1989_01_024.asd, Retrieved on: Feb. 7, 2012.
Oda, T. et al. "In Vivo Length-Force Relationships on Muscle Fiber and Muscle Tendon Complex in the Tibialis Anterior Muscle," *International Journal of Sport and Health Sciences*, 3:245-252 (2005).
Ogihara, N., and Yamazaki. N., "Generation of Human Bipedal Locomotion by a Bio-Mimetic Neuro-Musculo-Skeletal Model," *Biol. Cybern.*, 84: 1-11 (2001).
Palmer. M.L., "Sagittal Plane Characterization of Normal Human Ankle Function Across A Range of Walking Gait Speeds," Unpublished master's thesis, Massachusetts Institute of Technology, Massachusetts, 71 pages (2002).
Paluska, D., and Herr H., "The Effect of Series Elasticity on Actuator Power and Work Output: Implications for Robotic and Prosthetic Joint Design," Robotics and Autonomous Systems, 54:667-673 (2006).
Paluska, D., and Herr, H., "Series Elasticity and Actuator Power Output," paper presented at the Proceedings of the 2006 IEEE International Conference on Robotics and Automation, 4 pages (May 2006).
Pang, M.Y.C. and Yang, J.F., "The Initiation of the Swing Phase in Human Infact Stepping: Importance of Hip Position and Leg Loading," *Journal of Physiology*, 528(2):389-404 (2000).
Pasch, K.A., et al., "On the drive svstems for high performance machines." *AMSE J. Mechanisms, Transmissions, and Automation in Design* 106(1):102-108 (Mar. 1984).
Paul, C., et al., "Development of a Human Neuro-Musculo-Skeletal Model for Investigation of Spinal Cord Injury," *Biol. Cybern.*, 93:153-170 (2005).
Pearson, K., et al., "Assessing Sensory Function in Locomotor Systems Using neurp-mechanical Simulations," *Trends in Neurosciences*, 29(11): 626-631 (2006).
Pearson, K.G., "Generating the Walking Gait: Role of Sensory Feedback," *Progress in Brain Research*, 143:123-129 (2004).
Peeraer, L., et al., "Development of EMG-based mode and intent recognition algorithms for a computer-controlled above-knee prosthesis," J. Biomed. Eng., 12: 178-182 (1990).
Perry, J., et al., "Efficiency of Dynamic Elastic Response Prosthetic Feet," *Journal of Rehabilitation Research*, 30(1):137-143 (1993).
Petrofsky, J.S.., et al., "Feedback Control System for Walking in Man," *Comput. Biol. Med*. 14(2):135-149 (1984).

Pfeffer, L.E., et al., "Experiments with a Dual-Armed, Cooperative, Flexible-Drivetrain Robot System," paper presented at the IEEE, Aerospace Robotics Laboratory, Department of Aeronautics and Astronautics, Stanford University (1993).
Popovic, D. and Sinkjaer, T., "Control of Movement for the Physically Disabled: Control for Rehabilitation Technology," (Springer Publisher) pp. 270-302, No date given.
Popovic, D., et al., "Control Aspects of Active Above-Knee Prosthesis," *Int. J. Man-Machine Studies*, 35:751-767 (1991).
Popovic, M., et al., "Angular Momentum Primitives for Human Walking: Biomechanics and Control," paper presented at the Proceedings IEEE/RSJ International Conference on Intelligent Robots and Systems, Sendai, Japan, pp. 1685-1691 (2004).
Popovic, M., et al., "Angular Momentum Regulation During Human Walking: Biomechanics and Control," paper presented at the Proceedings IEEE International Conference on Robotics and Automation, New Orleans, LA, pp. 2405-2411 (2004).
Popovic, M., et al., "Conservation of Angular Momentum During Human Locomotion," *MIT Artificial Intelligence Laboratory*, pp. 231-232 (2002).
Popovic, M.B. and Herr, H., "Global Motion Control and Support Base Planning," MIT pp. 1-8, no date given.
Popovic, M.B. and Herr, H., "Ground Reference Points in Legged Locomotion: Definitions, Biological Trajectories and Control Implications," *Mobile Robots Towards New Applications*, ISBN 3-86611-314-5, pp. 79-104 (2006).
Popovic, M.B., et al., "Zero Spin Angular Momentum Control: Definition and Applicability," MIT, pp. 1-16, no date given.
Popovic, M.R., et al., "Gait Identification and Recognition Sensor," paper presented at the Proceedings of 6$^{th}$ Vienna International Workshop on Functional Electrostiumlation (Sep. 1998).
Pratt, G.A. and Williamson, M.M., "Series Elastic Actuators." Paper presented at the meeting of the IEEE, pp. 399-406 (1995).
Pratt, G.A., "Legged Robots at MIT: What's New Since Raibert." Paper presented at the meeting of the IEEE, Robotics and Automation Magazine (Sep. 2000).
Pratt, G.A., "Low Impedance Walking Robots," *Integ. and Comp. Biol.*, 42: 174-181 (2002).
Pratt, J.E., et al., "The RoboKnee: An Exoskeleton for Enhancing Strength and Endurance During Walking." Paper presented at the Proceedings of the 2004 IEEE International Conference on Robotics & Automation, New Orleans, LA (Apr. 2004).
Prochazka, A. and Yakovenko, S., "The Neuromechanical Tuning Hypothesis." *Progress in Brain Research*, 165: 257-267 (2007).
Prochazka, A., et al., "Positive Force Feedback Control of Muscles," *The American Physiological Society* 77:3226-3236 (1997).
Prochazka, A., et al., "Sensory Control of Locomotion: Reflexes Versus Higher-Level Control," *Sensorimotor Control of Movement and Posture*, pp. 357-367 (2002).
Raibert, M.H., "Legged Robots that Balance," MIT Press, Cambridge, MA, p. 89 (1985).
Rassier, D.E., et al., "Length Dependence of Active Force Production in Skeletal Muscle," *The American Physiological Society*, pp. 1445-1457 (1999).
Riener, R., et al., "Stair Ascent and Descent at Different Inclinations," *Gait and Posture*, 15: 32-44 (2002).
Rietman, J.S., et al., "Gait Analysis in Prosthetics: Opinions, Ideas and Conclusions," *Prosthetics and Orthotics International*, 26: 50-57 (2002).
Robinson, D.W., "Design and Analysis of Senes Elasticity in Closed-Loop Actuator Force Control." Unpublished doctoral dissertation, Massachusetts Institute of Technology (2000).
Robinson, D.W., et al., "Series Elastic Actuator Development for a Biomimetic Walking Robot." Paper presented at the IEEE/ASME International Conf. on Adv. Intelligent Mechatronics (Sep. 19-22, 1999).
Rosen, J., et al., "A Myosignal-Based Powered Exoskeleton System," *IEEE Transaction on Systems, Man. and Cybernetics—Part A: Systems and Humans*, 31(3):210-222 (2001).
Ruina, A., et al., "A Collisional Model of the Energetic Cost of Support Work Qualitatively Explains Leg Sequencing in Walking

(56) References Cited

OTHER PUBLICATIONS and Galloping. Pseudo-Elastic Leg Behavior in Running and the Walk-To-Run Transition," *J. of Theoretical Biology*, 237: 170-192 (2005).
Rybak, I.A., et al., "Modelling Spinal Circuitry Involved in Locomotor Pattern Generation: Insights from Deletions During Fictive Locomotion," *J. Physiol.*, 577(2):617-639 (2006).
Rybak, I.A., et al., "Modelling Spinal Circuitry Involved in Locomotor Pattern Generation: Insights from the Effects of Afferent Stimulation," *J. Physiol.*, 577(2):641-658 (2006).
Sanderson, D.J. and Martin. P.E., "Lower Extremity Kinematic and Kinetic Adaptations in Unilateral Below-Knee Amputees During Walking," *Gait & Posture*, 6(2): 126-136 (1997).
Sanger, T.D., "Human Arm Movements Described by a Low-Dimensional Superposition of Principal Components," *The J. of Neuroscience*, 20(3):1066-1072 (2000).
Saranli, U., et al., "RHex: A Simple and Highly Mobile Hexapod Robot," *The International Journal of Robotics Research*, pp. 616-631 (2001).
Sarrigeorgidis, K. and Kyriakopoulos, K.J., "Motion Control of the N.T.U.A. Robotic Snake on a Planar Surface." Paper presented at the Proceedings of the 1998 IEEE International Conference on Robotics & Automation, Leuven, Belgium (May 1998).
Saxena, S. C., and Mukhopadhyay, P., "E.M.G. operated electronic artificial-leg controller," Med. & Biol. Eng. & Comput., 15: 553-557 (1977).
Schaal, S. and Atkeson, C.G., "Constructive Incremental Learning from Only Local Information," *Neural Computation*, 10(8): 2047-2084 (1998).
Schaal, S., "Is Imitation Learning the Route to Humanoid Robots?", *Trends in Cognitive Sciences*, 3: 233-242 (1999).
Scott, S.H. and Winter, D.A., "Biomechanical Model of the Human Foot: Kinematics and Kinetics During the Stance Phase of Walking," *J. Biomechanic*, 26(9): 1091-1104 (1993).
Sentis, L. and Khatib, O., "Task-Oriented Control of Humanoid Robots Through Prioritization." Paper presented at the IEEE-RAS/RSJ International Conference on Humanoid Robots, pp. 1-16 (no date given).
Seyfarth, A., et al., "A Movement Criterion for Running," *J. of Biomechanics*, 35: 649-655 (2002).
Seyfarth, A., et al., "Stable Operation of an Elastic Three-Segment Leg," *Biol. Cybern.*, 84: 365-382 (2001).
Seyfarth, A., et al., "Swing-Leg Retraction: A Simple Control Model for Stable Running," *The J. of Experimental Biology*, 206: 2547-2555 (2003).
Sinkjaer, T., et al., "Major role for sensory feedback in soleus EMG activity in the stance phase of walking in man," *Journal of Physiology*, 523.3: 817-827 (2000).
Skinner, H.B., and Effeney, D.J., "Gait Analysis in Amputees," *American Journal of Physical Medicine*, 64(2): 82-89 (1985).
Smidt, G.L., et al., "An Automated Accelerometry System For Gait Analysis," *J. Biomechanics*, 10: 367-375 (1977).
Srinivasan, M., "Energetics of Legged Locomotion: Why is Total Metabolic Cost Proportional to the Cost of Stance Work." ISB XXth Congress—ASB 29$^{th}$ Annual Meeting, Cleveland, OH (Jul. 31-Aug. 5 (no year given).
Stepien, J., et al., "Activity Levels Among Lower-Limb Amputees: Self-Report Versus Step Activity Monitor," *Arch. Phys. Med. Rehabil.*, 88: 896-900 (2007).
Sugano, S. et al., "Force Control of the Robot Finger Joint equipped with Mechanical Compliance Adjuster," Proceedings of the 1992 IEEE/RSJ International Conference on Intelligent Robots and Systems, Raleigh, NC (Jul. 1992).
Sugihara, T., et al., "Realtime Humanoid Motion Generation through ZMP Manipulation based on Inverted Pendulum Control," Proceedings of the 2002 IEEE International Conference on Robotics & Automation, Washington, DC (May 2002).
Sup, F., et al., "Design and Control of a Powered Transfemoral Prosthesis," *The International Journal of Robotics Research*, 27(2): 263-273 (2008).

Supplementary European Search Report Application No. 10736533. 0, "Powered Artificial Knee with Agonist-Antagonist Actuation," dated Aug. 16, 2013.
Supplementary European Search Report Application No. 10736550. 0, "Model-Based Neuromechanical Controller for a Robotic Leg," dated Aug. 1, 2013.
Taga, G., "A model of the neuro-musculo-skeletal system for human locomotion," *Biol. Cybern.*, 73: 97-111 (1995).
Takayuki, F., et al., "Biped Locomotion using Multiple Link Virtual Inverted Pendulum Model," *T.IEE Japan*, 120-C (2): 208-214 (2000).
Thoroughman, K., and Shadmehr, R., "Learning of action through adaptive combination of motor primitives," *Nature*, 407: 742-747(2000).
Tomovic, R., and McHee, R.B., "A Finite State Approach to the Synthesis of Bioengineenng Control Systems," *IEEE Transactions on Human Factors in Electronics*, 7(2): 65-69 (1966).
Tong. K., and Granat, M., "A practical gait analysis system using gyroscopes," *Medical Engineering & Physics*, 21: 87-94 (1999).
Türker, K., "Electromyography: Some Methodological Problems and Issues," *Phys. Ther.*, 73: 698-710 (1993).
Van den Bogert, A. J., "Exotendons for Assistance of Human Locomotion," Biomedical Engineering OnLine, BioMed Central, 2(17):1-8 (2003).
Van den Bogert, A. J., et al., "A Method for Inverse Dynamic Analysis Using Accelerometry," *J. Biochemechanics*, 29(7): 949-954 (1996).
Veltink, P.H., et al., "Tire Feasibility of Posture and Movement Detection by Accelerometry," paper presented at the IEEE meeting (1993).
Vukobratovic, M., and Juricic, D., "Contribution to the Synthesis of Biped Gait," paper presented at the IEEE Transactions on Bio-Medical Engineering, BME-16(1) (Jan. 1969).
Vukobratovic, M., and Stepanenko, J., Mathematical Models of General Anthropomorphic Systems, *Mathematical Biosciences*, 17: 191-242(1973).
Walsh, C.J., et al., "Biomimetic Design of an Under-Actuated Leg Exoskeleton for Load-Carrying Augmentation," Unpublished Master's thesis, Massachusetts Institute of Technology, Cambridge, MA (2006).
Waters, R.L., et al., "Energy Cost of Walking of Amputees: The Influence of Level of Amputation," *The Journal of Bone and Joint Surgery*, 58A(1): 42-46 (1976).
Wilkenfeld, A., "Biologically Inspired Autoadaptive Control of a Knee Prosthesis," unpublished doctoral dissertation, Massachusetts Institute of Technology, Cambridge, MA (2000).
Wilkenfeld, A., and Herr, H., "An Auto-Adaptive External Knee Prosthesis," MIT Lab., (No date given).
Willemsen, A.Th.M., et al., "Automatic Stance-Swing Phase Detection from Accelerometer Data for Peroneal Nerve Stimulation," presented at the meeting of IEEE Transactions on Biomedical Engineenng, 37(12):1201-1208 (1990).
Willemsen. A.Th.M., et al., "Real-Time Gait Assessment Utilizing A New Way of Accelerometry," *J. Biomechanics*, 23(8):859-863 (1990).
Williams, B.C., et al., "Mode Estimation of Model-Based Programs: Monitoring Systems with Complex Behavior," paper submitted to Massachusetts Institute of Technology, Cambridge, MA, (No date given).
Williamson, M.M., "Series Elastic Actuators." A.I. Technical Report # 1524 submitted to Massachusetts Institute of Technology, Cambridge, Massachusetts (Jan. 1995).
Winter, D.A., "Energy Generation and Absorption at the Ankle and Knee during Fast, Natural, and Slow Cadences," *Clinical Orthopedics and Related Research*, 175: 147-154 (1983).
Winter, D.A., and Robertson, D.G.E., "Joint Torque and Energy Patterns in Normal Gait," Biol. Cybernetics, 29:137-142 (1978).
Winter, D.A., and Sienko, S.E., "Biomechanics of Below-Knee Amputee Gait," *J. Biomechanics*, 21(5):361-367 (1988).
Wisse, M., "Essentials of Dynamic Walking: Analysis and Design of Two-legged Robots," 195 pgs, (2004).

(56) References Cited

OTHER PUBLICATIONS

Woodward, M.I. and Cunningham, J.L., "Skeletal Accelerations Measured During Different Exercises," *Proc. Instn. Mech. Engrs.*, 207: 79-85 (1993).

Wu, G. and Ladin, Z., "The Study of Kinematic Transients in Locomotion Using the Integrated Kinematic Sensor," *IEEE Transactions on Rehabilitation Engineering*, 4(3):193-200 (1996).

Yakovenko, S., et al., "Contribution of Stretch Reflexes to Locomotor Control: A Modeling Study," *Biol. Cybern.*, 90: 146-155 (2004).

Yun, X., "Dynamic State Feedback Control of Constrained Robot Manipulators." Paper presented at the Proceedings of the $27^{th}$ Conference on Decision and Control, Austin, TX (Dec. 1988).

Zlatnik, D., et al., "Finite-State Control of a Trans-Femoral (TF) Prosthesis," *IEEE Transactions on Control Systems and Technology*, 10(3): 408-420 (2002).

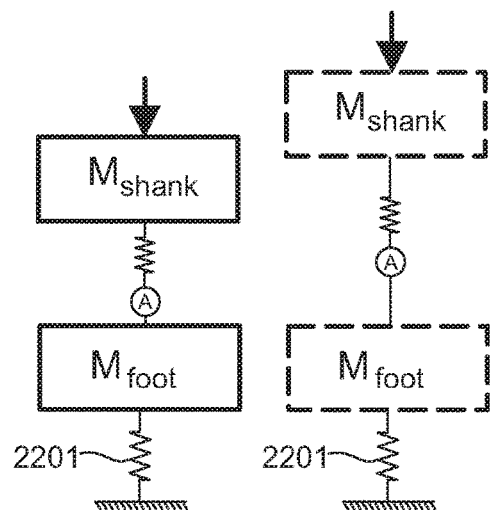
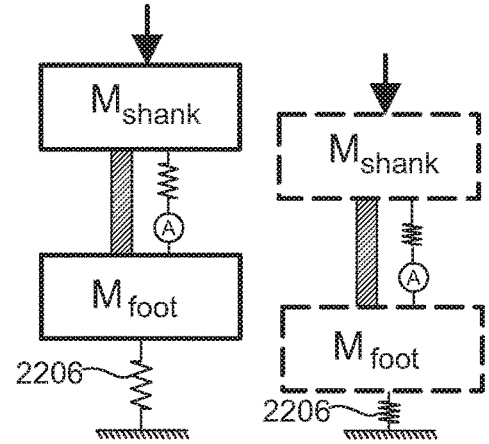

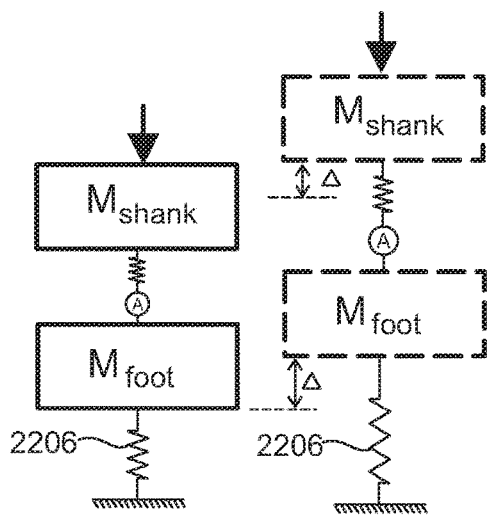
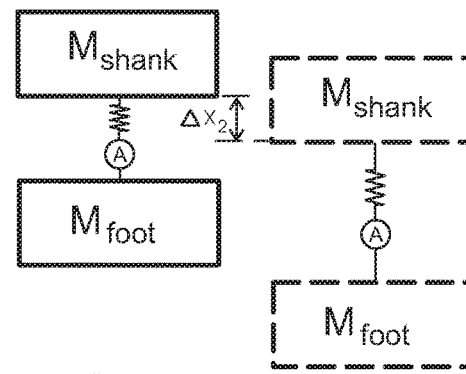

ARTIFICIAL ANKLE-FOOT SYSTEM WITH SPRING, VARIABLE-DAMPING, AND SERIES-ELASTIC ACTUATOR COMPONENTS

This application is a divisional of U.S. application Ser. No. 15/091,895, filed Apr. 6, 2016, now U.S. Pat. No. 10,342,681, which is a continuation of U.S. application Ser. No. 14/283,323, filed May 21, 2014, now U.S. Pat. No. 9,339,397, which is a divisional of U.S. application Ser. No. 13/723,743, filed Dec. 21, 2012, now U.S. Pat. No. 8,734,528, which is a continuation of U.S. application Ser. No. 13/348,570, filed Jan. 11, 2012, now abandoned, which is a continuation of U.S. patent application Ser. No. 11/495,140, filed Jul. 29, 2006, now abandoned, which is a non-provisional of, and also claims the benefit of the filing date of, U.S. Provisional Patent Application No. 60/704,517 filed on Aug. 1, 2005, each of which is herein incorporated by reference.

U.S. patent application Ser. No. 11/495,140 is a continuation-in-part of, and claims the benefit of the filing date of, U.S. patent application Ser. No. 11/395,448 filed on Mar. 31, 2006, now abandoned. Application Ser. No. 11/395,448 was a non-provisional of, and claimed the benefit of the filing date of, U.S. Provisional Patent Application No. 60/666,876 filed on Mar. 31, 2005 and U.S. Provisional Patent Ser. No. 60/704,517 filed on Aug. 1, 2005, each of which is herein incorporated by reference.

This application incorporates the disclosures of each of the foregoing applications herein by reference.

FIELD OF THE INVENTION

This invention relates generally to prosthetic devices and artificial limb and joint systems, including robotic, orthotic, exoskeletal limbs, and more particularly, although in its broader aspects not exclusively, to artificial feet and ankle joints.

BACKGROUND OF THE INVENTION

In the course of the following description, reference will be made to the papers, patents and publications presented in a list of references at the conclusion of this specification. When cited, each listed reference will be identified by a numeral within curly-braces indicating its position within this list.

As noted in {1}{2}{3}, an artificial ankle-foot system ideally needs to fulfill a diverse set of requirements. The artificial system must be a reasonable weight and have a natural morphological shape, but still have an operational time between refueling or battery recharges of at least one full day. The system must also be capable of varying its position, impedance, and motive power in a comparable manner to that of a normal, healthy biological limb. Still further, the system must be adaptive, changing its characteristics given such environmental disturbances as walking speed and terrain variation. The embodiments of the invention that are described in this specification employ novel architectures capable of achieving these many requirements.

From recent biomechanical studies {1}{2}{3}, researchers have determined researchers have determined that early stance period ankle stiffness varies from step-to-step in wag. Furthermore, researchers have discovered that the human ankle performs more positive mechanical work than negative work, especially at moderate to fast wag speeds {1}{2}{3}. The added ankle power is important for providing adequate forward progression of the body at the end of each stance period. In distinction, for stair descent, the ankle behaves as a variable damper during the first half of stance, absorbing impact energies {2}. These biomechanical findings suggest that in order to mimic the actual behavior of the human ankle, joint stiffness, motive power, and damping must be actively controlled in the context of an efficient, high cycle-life, quiet and cosmetic ankle-foot artificial joint.

For level ground ambulation, the ankle behaves as a variable stiffness device during the early to midstance period, storing and releasing impact energies. Throughout terminal stance, the ankle acts as a torque source to power the body forward. In distinction, the ankle varies damping rather than stiffness during the early stance period of stair descent. These biomechanical findings suggest that in order to mimic the actual behavior of a human joint or joints, stiffness, damping, and nonconservative, motive power must be actively controlled in the context of an efficient, high cycle-life, quiet and cosmetic biomimetic limb system, be it for a prosthetic or orthotic device. This is also the case for a biomimetic robotic limb since it will need to satisfy the same mechanical and physical laws as its biological counterpart, and will benefit from the same techniques for power and weight savings.

In the discussion immediately below, the biomechanical properties of the ankle will be described in some detail to explain the insights that have guided the design and development of the specific embodiments of the invention and to define selected terms that will be used in this specification.

Joint Biomechanics: The Human Ankle

Understanding normal walking biomechanics provides the basis for the design and development of the artificial ankle joint and ankle-foot structures that embody the invention. Specifically, the function of human ankle under sagittal plane rotation is described below for different locomotor conditions including level-ground walking and stair/slope ascent and descent. From these biomechanical descriptions, the justifications for key mechanical components and configurations of the artificial ankle structures and functions embodying the invention may be better understood.

Level-Ground Walking

A level-ground walking gait cycle is typically defined as beginning with the heel strike of one foot and ending at the next heel strike of the same foot {8}. The main subdivisions of the gait cycle are the stance phase (about 60% of the cycle) and the subsequent swing phase (about 40% of the cycle) as shown in FIG. 1. The swing phase represents the portion of the gait cycle when the foot is off the ground. The stance phase begins at heel-strike when the heel touches the floor and ends at toe-off when the same foot rises from the ground surface. Additionally, we can further divide the stance phase into three sub-phases: Controlled Plantar flexion (CP), Controlled Dorsiflexion (CD), and Powered Plantar flexion (PP).

Each phase and the corresponding ankle functions which occur when walking on level ground are illustrated in FIG. 1. The subdivisions of the stance phase of walking, in order from first to last, are: the Controlled Plantar flexion (CP) phase, the Controlled Dorsiflexion (CD) phase, and the Powered Plantar flexion (PP) phase.

CP begins at heel-strike illustrated at 103 and ends at foot-flat at 105. Simply speaking, CP describes the process by which the heel and forefoot initially make contact with the ground. In {1, 12}, researchers showed that CP ankle joint behavior was consistent with a linear spring response where joint torque is proportional to joint position. The spring behavior is, however, variable; joint stiffness is continuously modulated by the body from step to step.

After the CP period, the CD phase continues until the ankle reaches a state of maximum dorsiflexion and begins powered plantarflexion PP as illustrated at 107. Ankle torque versus position during the CD period can often be described as a nonlinear spring where stiffness increases with increasing ankle position. The main function of the ankle during CD is to store the elastic energy necessary to propel the body upwards and forwards during the PP phase {9}{3}.

The PP phase begins after CD and ends at the instant of toe-off illustrated at 109. During PP, the ankle can be modeled as a catapult in series or in parallel with the CD spring or springs. Here the catapult component includes a motor that does work on a series spring during the latter half of the CD phase and/or during the first half of the PP phase. The catapult energy is then released along with the spring energy stored during the CD phase to achieve the high plantar flexion power during late stance. This catapult behavior is necessary because the work generated during PP is more than the negative work absorbed during the CP and CD phases for moderate to fast walking speeds {1}{2}{3}{9}.

During the swing phase, the final 40% of the gait cycle, which extends from toe-off at 109 until the next heel strike at 113, the foot is lifted off the ground.

Stair Ascent and Descent

Because the kinematic and kinetic patterns at the ankle during stair ascent/descent are significantly different from that of level-ground walking {2}, a separate description of the ankle-foot biomechanics is presented in FIGS. 2 and 3.

FIG. 2 shows the human ankle biomechanics during stair ascent. The first phase of stair ascent is called Controlled Dorsiflexion 1 (CD 1), which begins with foot strike in a dorsiflexed position seen at 201 and continues to dorsiflex until the heel contacts the step surface at 203. In this phase, the ankle can be modeled as a linear spring.

The second phase is Powered Plantar flexion 1 (PP 1), which begins at the instant of foot flat (when the ankle reaches its maximum dorsiflexion at 203) and ends when dorsiflexion begins once again at 205. The human ankle behaves as a torque actuator to provide extra energy to support the body weight.

The third phase is Controlled Dorsiflexion 2 (CD 2), in which the ankle dorsiflexes until heel-off at 207. For the CD 2 phase, the ankle can be modeled as a linear spring.

The fourth and final phase is Powered Plantar flexion 2 (PP 2) which begins at heel-off 207 and continues as the foot pushes off the step, acting as a torque actuator in parallel with the CD 2 spring to propel the body upwards and forwards, and ends when the toe leaves the surface at 209 to being the swing phase that ends at 213.

FIG. 3 shows the human ankle-foot biomechanics for stair descent. The stance phase of stair descent is divided into three sub-phases: Controlled Dorsiflexion 1 (CD1), Controlled Dorsiflexion 2 (CD2), and Powered Plantar flexion (PP).

CD1 begins at foot strike illustrated at 303 and ends at foot-flat 305. In this phase, the human ankle can be modeled as a variable damper. In CD2, the ankle continues to dorsiflex forward until it reaches a maximum dorsiflexion posture seen at 307. Here the ankle acts as a linear spring, storing energy throughout CD2. During PP, which begins at 307, the ankle plantar flexes until the foot lifts from the step at 309. In this final PP phase, the ankle releases stored CD2 energy, propelling the body upwards and forwards. After toe-off at 309, the foot is positioned controlled through the swing phase until the next foot strike at 313.

For stair ascent depicted in FIG. 2, the human ankle-foot can be effectively modeled using a combination of an actuator and a variable stiffness mechanism. However, for stair descent, depicted in FIG. 3, a variable damper needs also to be included for modeling the ankle-foot complex; the power absorbed by the human ankle is much greater during stair descent than the power released by 2.3 to 11.2 J/kg {2}. Hence, it is reasonable to model the ankle as a combination of a variable-damper and spring for stair descent {2}.

SUMMARY OF THE INVENTION

The preferred embodiments of the present invention take the form of an artificial ankle system capable of providing biologically-realistic dynamic behaviors. The key mechanical components of these embodiments, and their general functions, may be summarized as follows:

1. One or more passive springs—to store and release elastic energy for propulsion;
2. One or more series-elastic actuators (muscle-tendon)—to control the position of the ankle, provide additional elastic energy storage for propulsion, and to control joint stiffness; and
3. One or more variable dampers—to absorb mechanical energy during stair and slope descent.

The above-identified U.S. patent application Ser. No. 11/395,448 filed on Mar. 31, 2006 describes related artificial limbs and joints that employ passive and series-elastic elements and variable-damping elements, and in addition employ active motor elements in arrangements called "Biomimetic Hybrid Actuators" forming biologically-inspired musculoskeletal architectures. The electric motor used in the hybrid actuators supply positive energy to and store negative energy from one or more joints which connect skeletal members, as well as elastic elements such as springs, and controllable variable damper components, for passively storing and releasing energy and providing adaptive impedance to accommodate level ground walking as well as movement on stairs and surfaces having different slopes.

As described in application Ser. No. 11/395,448, an artificial ankle may employ an elastic member operatively connected in series with the motor between the shin member and the foot member to store energy when the relative motion of the foot and shin members is being arrested by a controllable variable damping element and to thereafter apply an additional torque to the ankle joint when the variable damping element no longer arrests the relative motion of the two members.

As further described in application Ser. No. 11/395,448, an artificial ankle may include an elastic member operatively connected in series with the motor between the shin and foot members to store energy when the foot member is moved toward the shin member and to release energy and apply an additional torque to the ankle joint that assists the motor to move the foot member away from the shin member. A controllable damping member may be employed to arrest the motion of the motor to control the amount of energy absorbed by the motor when the foot member is moved toward the shin member.

The Flex-Foot, made by Össur of Reykjavik, Iceland, is a passive carbon-fiber energy storage device that replicates the ankle joint for amputees. The Flex-Foot is described in U.S. Pat. No. 6,071,313 issued to Van L. Phillips entitled "Split foot prosthesis" and in Phillips' earlier U.S. Pat. Nos. 5,776,205, 5,514,185 and 5,181,933, the disclosures of which are incorporated herein by reference. The Flex-foot is a foot prosthesis for supporting an amputee relative to a support surface and consists of a leaf spring having multiple flexing portions configured to flex substantially independently of one another substantially completely along their length. The Flex-Foot has an equilibrium position of 90 degrees and a single nominal stiffness value. In the embodiments described below, a hybrid actuator mechanism of the kind described in the above-noted application Ser. No. 11/395,448 is used to augment a flexing foot member such as the Flex-Foot by allowing the equilibrium position to be set to an arbitrary angle by a motor and locking, or arresting the relative movement of, the foot member with respect to the shin member using a clutch or variable damper. Furthermore, the embodiment of the invention to be described can also change the stiffness and damping of the prosthesis dynamically.

Preferred embodiments of the present invention take the form of an artificial ankle and foot system in which a foot and ankle structure is mounted for rotation with respect to a shin member at an ankle joint. The foot and ankle structure preferably comprises a curved flexible elastic foot member that defines an arch between a heel extremity and a toe extremity, and a flexible elastic ankle member that connects said foot member for rotation at the ankle joint. A variable damper is employed to arresting the motion of said foot and ankle structure with respect to said shin member under predetermined conditions, and preferably includes a stop mechanism that prevents the foot and ankle structure from rotating with respect to the shin member beyond a predetermined limit position. The variable damper may further include a controllable damper, such as a magnetorheological (MR) brake, which arrests the rotation of the ankle joint by controllable amount at controlled times during the walking cycle. Preferred embodiments of the ankle and foot system further include an actuator motor for applying torque to the ankle joint to rotate said foot and ankle structure with respect to said shin member.

In addition, embodiments of the invention may include a catapult mechanism comprising a series elastic member operatively connected in series with the motor between the shin member and the foot and ankle structure. The series elastic member stores energy from the motor during a first portion of each walking cycle and then releases the stored energy to help propel the user forward over the support surface at a later time in each walking cycle. The preferred embodiments of the invention may employ a controller for operating both the motor and the controllable damper such that the motor stores energy in the series elastic member as the shin member is being arrested by the controllable damper.

The actuator motor which applies torque to the ankle joint may be employed to adjust the position of the foot and ankle structure relative to the shin member when the foot and ankle member is not in contact with a support surface. Inertial sensing means are preferably employed to determine the relative elevation of the foot and angle structure and to actuate the motor in response to changes in the relative elevation, thereby automatically positioning the foot member for toe first engagement if the wearer is descending stairs.

These and other features and advantages of the present invention will be better understood by considering the following detailed description of two illustrative embodiments of the invention. In course of this description, frequent reference will be made to the attached drawings, which are briefly described below.

DETAILED DESCRIPTION OF THE INVENTION

Two embodiments of an ankle-foot system contemplated by the present invention are described in detail below. The first embodiment (Embodiment 1) provides for elastic energy storage, variable-damping and a variable-orientation foot control. In addition to these capabilities, the second embodiment to be described includes a motor in series with a spring for providing joint spring stiffness control during the CP and CD phases, and a motive torque control during the PP phase of the walking cycle as described above.

Embodiment 1

Mechanical Components

Figure 1:
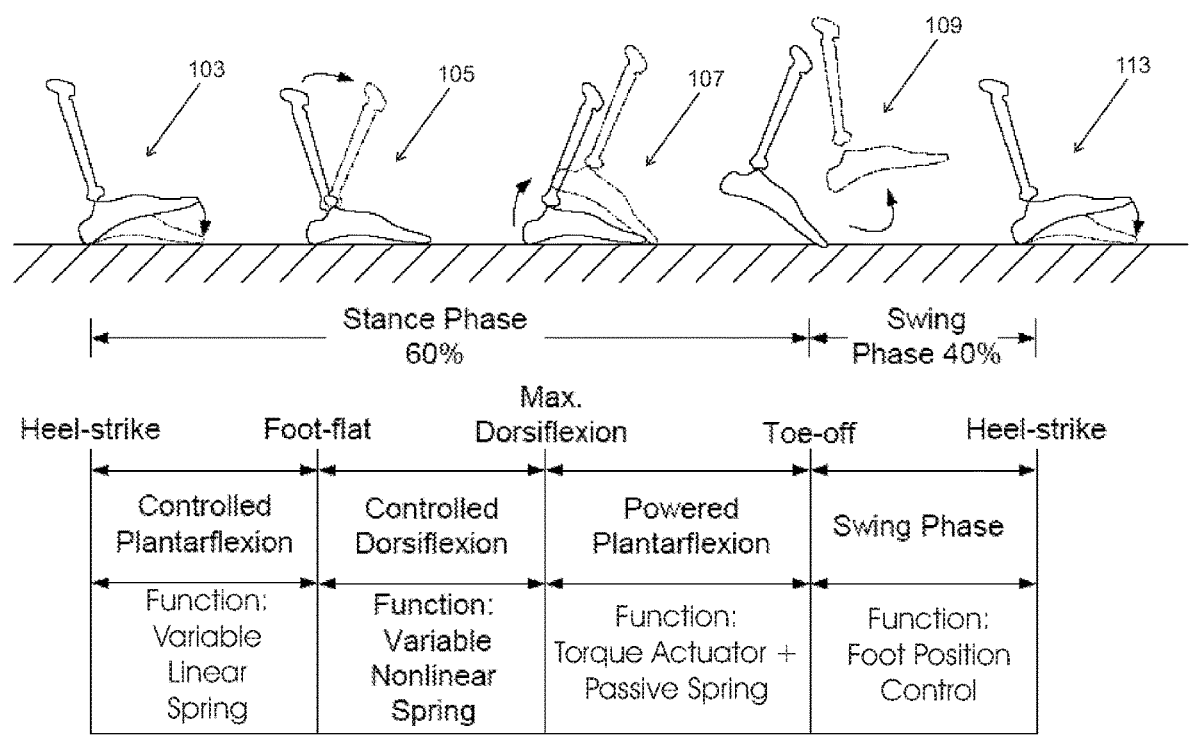
FIG. 1 illustrates the different phases of a walking cycle experienced by a human ankle and foot during level ground walking.
Figure 2:
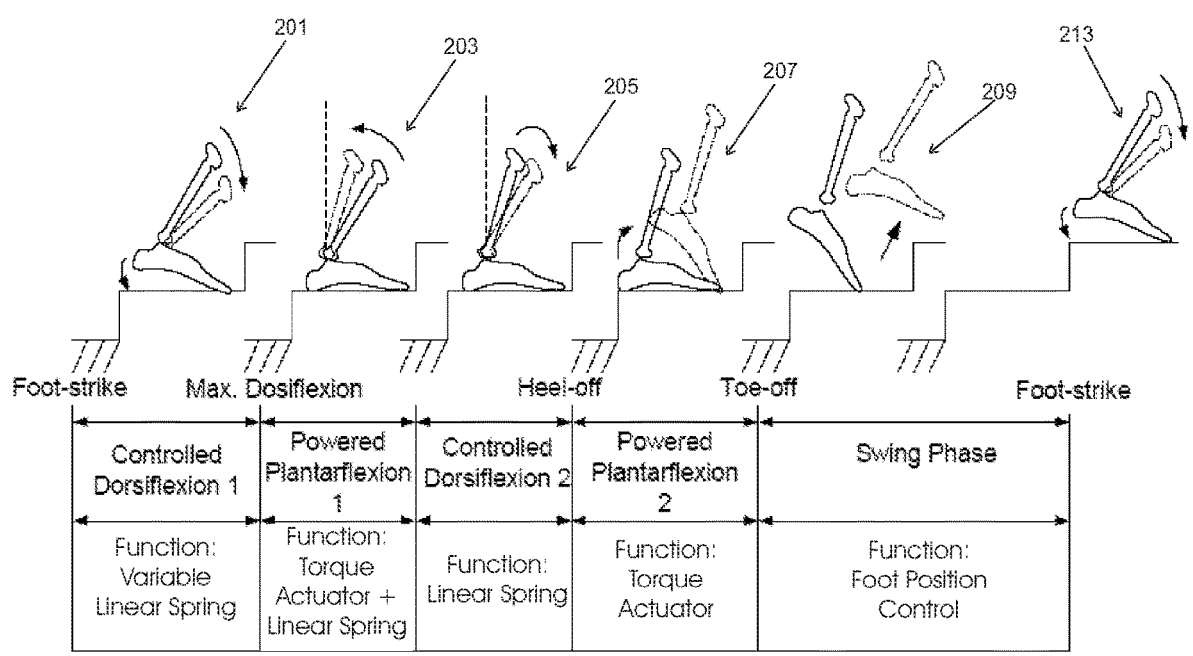
FIG. 2 depicts the phases of a walking cycle experienced by a human ankle and foot when ascending stairs.
Figure 3:
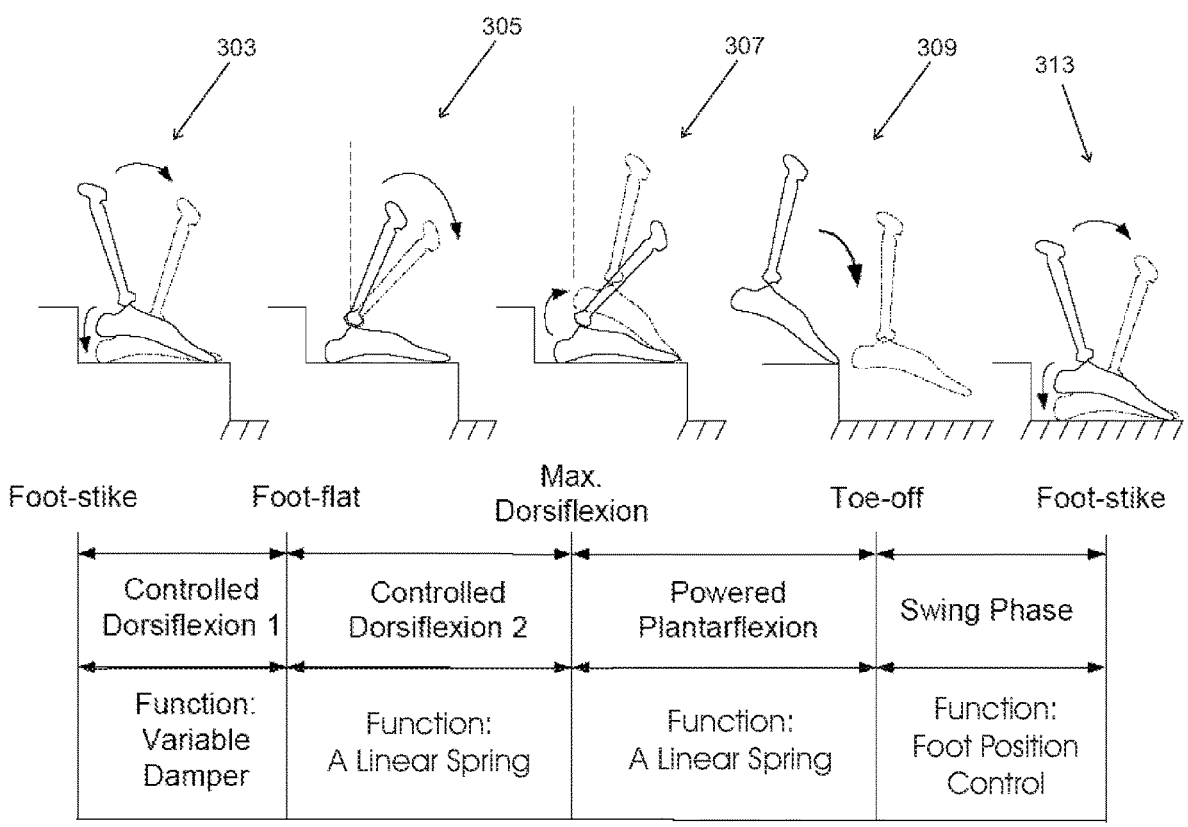
FIG. 3 depicts the phases of a walking cycle experienced by a human ankle and foot during stair descent.
Figure 4:
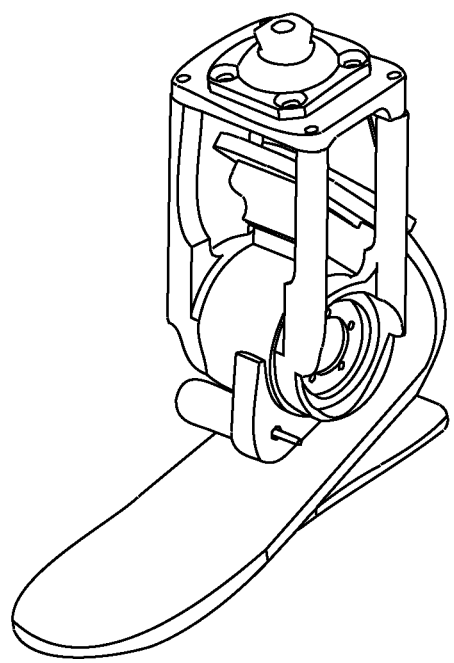
FIG. 4 shows the mechanical design of an anterior view of embodiment 1.
Figure 5:
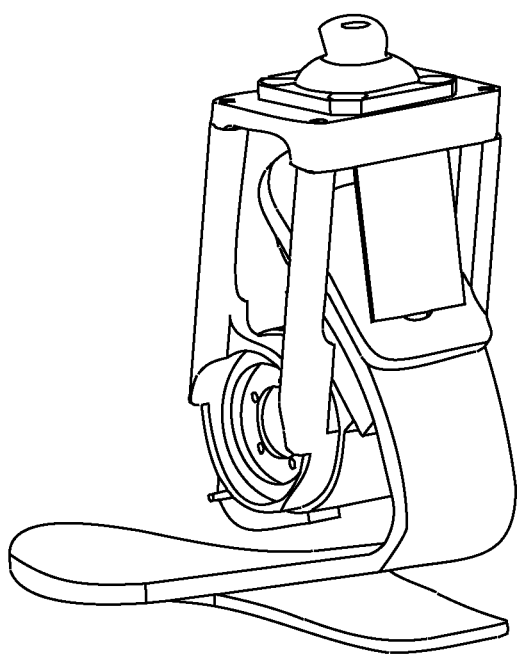
FIG. 5 shows a posterior view of embodiment 1.
Figure 6:
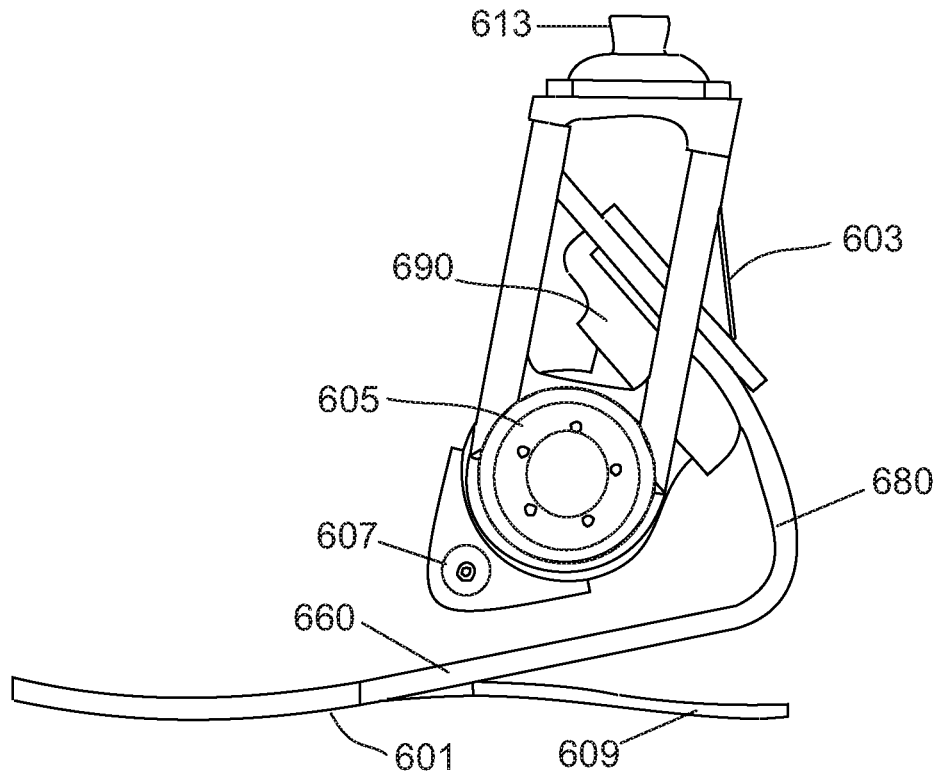
FIG. 6 shows a side elevational view of embodiment 1.
Figure 7:
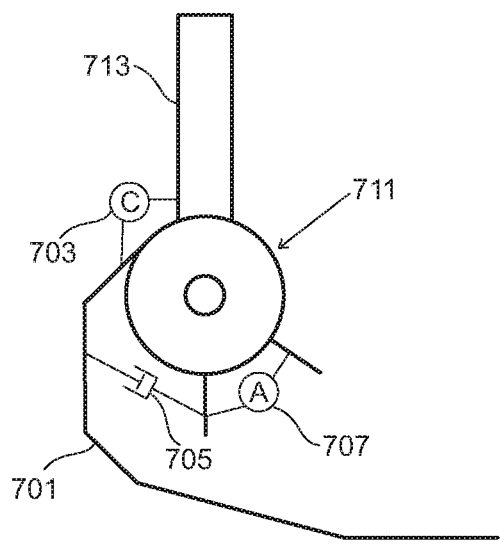
FIG. 7 is a schematic depiction of embodiment 1.
Figure 8:
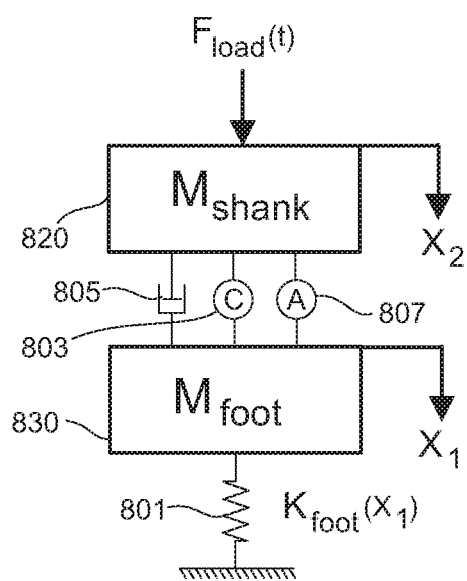
FIG. 8 depicts a lumped parameter model of embodiment 1.
Figure 9:
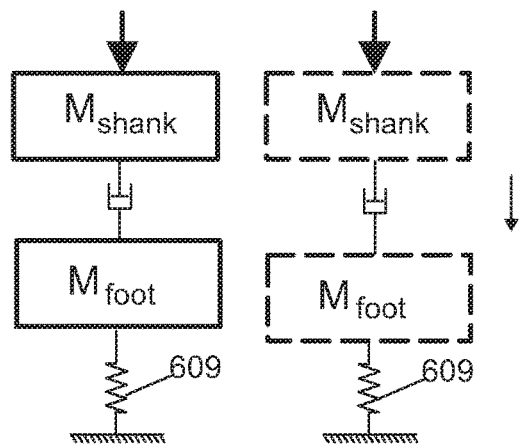
FIGS. 9-12 show the control sequence for embodiment 1 during ground level walking.
Figure 9:
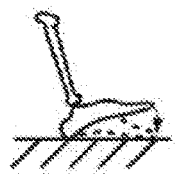

The mechanical design of embodiment 1 is seen in FIGS. 4-6 and the corresponding schematic and lumped parameter model of embodiment 1 are shown in FIGS. 7 and 8, respectively. As seen in the side elevation view of FIG. 6, there are four main mechanical elements in this embodiment: an elastic leaf spring structure 601, a dorsiflexion clutch (Ribbon Stop) seen at 603, a variable damper (MR brake) seen at 605, and an actuator system comprising a small motor seen at 607. As seen in the schematic of FIG. 7, these four main mechanical elements are shown as an elastic leaf spring structure 701, a dorsiflexion clutch (Ribbon Stop) 703, a variable damper 705, and a motor actuator system 707.

The elastic leaf spring seen at 601 and 701 can be made from a lightweight, efficient spring material such as carbon composite, fiberglass or a material of similar properties. As seen in FIG. 6, and as described in Phillips' U.S. Pat. No. 6,071,313 issued on Jun. 6, 2000, the elastic leaf spring structure includes a heel portion seen at 609 and a toe portion seen at 660. A curved, flexible ankle section 680 is attached at its upper end to a brake mount member 690 which is mounts the flexible foot for rotation about the axis of the ankle joint which, in FIG. 6, is located at the center of the MR brake 605.

The variable-damper mechanism seen at 605 and 705 can be implemented using magnetorheological (MR), electrorheological (ER), dry magnetic particles, hydraulic, pneumatic, friction, or any similar strategy to control joint damping. For embodiment 1, a MR system is employed. Here MR fluid is used in the shear mode where a set of rotary plates shear thin layers of MR fluid. When a magnetic field is induced across the MR layers, iron particles suspended in carrier fluid form chains, increasing the shear viscosity and joint damping.

The ribbon stop seen at 603 and 703 prevents the ankle joint from dorsiflexing beyond a certain maximum dorsiflexion limit, ranging from 0 to 30 degrees depending on ankle performance requirements. The ribbon stop is unidirectional, preventing dorsiflexion but not impeding plantarflexion movements.

The actuator motor seen at 607 and 707 is a small, low-power electromagnetic motor that provides foot orientation control. The motor can exert a torque about the ankle joint (indicated at 711) to re-position the foot (the elastic leaf spring 601, 701) relative to the shank depicted at 713 when the foot is not in contact with the ground. As seen in FIGS. 4-6, the shank frame for the ankle-foot assembly attaches to a shin member (not shown) using a standard pyramid mount seen at 613 which may be used to attach the shank frame to the shin portion of an artificial limb or the wearer's stump. As will be understood, both of the artificial foot and ankle joint embodiments described in this specification may be used in combination with artificial limb structures such as the artificial knees and hips described in the above-noted U.S. patent application Ser. No. 11/395,448.

Control System

For a better understanding of the control sequence of the artificial ankle, a simplified 1D lumped parameter model of embodiment 1 seen in FIG. 8 is used to explain the behavior of the ankle-foot system under different walking conditions.

From FIG. 7, it may be noted that the bending angle of the elastic leaf spring 701 is independent of the ankle angle of the pin joint, therefore the lumped parameter model includes two degrees of freedom: one for the displacement of the foot, $X_1$, and the other for the displacement of the shank $X_2$ as shown in FIG. 8. The leaf spring structure, seen at 601 in FIG. 6 and at 701 in FIG. 7, is modeled as a nonlinear spring shown at 801 in FIG. 8 with a stiffness that varies with $X_1$, the foot bending angle (displacement of the foot). The actuator motor seen at 807, the variable-damper 805, and the ribbon stop seen at 803 act between the mass of the shank at 820 and the mass of the foot at 830. The loading force $F_{load}(t)$ due to body weight varies dynamically during the stance phase of each gait cycle.

Level-Ground Walking

Figure 10:
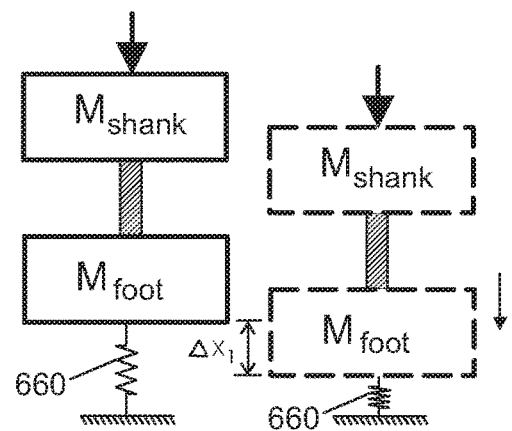
Figure 10:
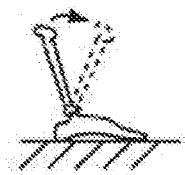
Figure 11:
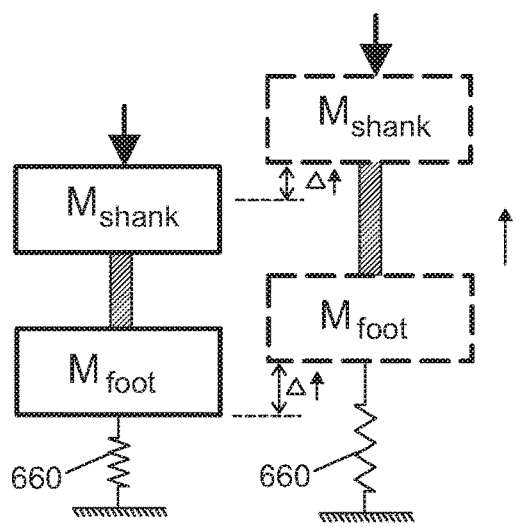
Figure 11:
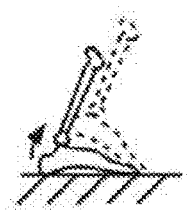
Figure 12:
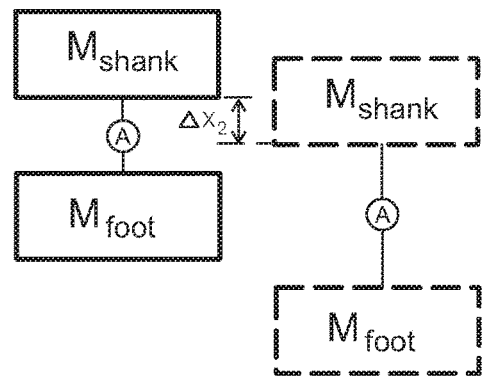
Figure 12:
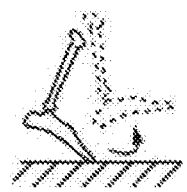

The control sequence of Embodiment 1 for level-ground walking is depicted in FIGS. 9-12. During level-ground walking, the variable-damper is set at a high damping level to essentially lock the ankle joint during early to midstance, allowing the leaf spring structure to store and release elastic energy. Once a critical dorsiflexion angle is achieved (between 0 to 30 degrees), the ribbon stop becomes taught during the remainder of the CD phase. When the ribbon is engaged, the leaf spring and shank can be treated as one single component because the ribbon behaves as a clutch (FIG. 10). From heel strike to maximum dorsiflexion, the leaf spring structure stores elastic energy ($\Delta X_1 \leq 0$, $\Delta X_2 = 0$). In PP, as the loading from the body weight decreases, the spring structure releases its stored elastic energy, rotating in a plantar flexion direction and propelling the body upwards and forwards (FIG. 11). After toe-off, the actuator controls the equilibrium position of the foot to achieve foot clearance during the swing phase and to maintain a proper landing of the foot for the next gait cycle (FIG. 12).

The state of each element of the ankle-foot system during the four phases of a level ground walking cycle are listed below:

Controlled Plantar Flexion (FIG. 9)
1. Actuator motor is OFF
2. Ribbon clutch is OFF
3. Damper is ON
4. Leaf spring heel portion at 609 is being compressed Controlled Dorsiflexion (FIG. 10)
1. Actuator motor is OFF
2. Ribbon clutch is ON
3. Damper is OFF
4. Leaf spring toe section 660 is being compressed Powered Plantar Flexion (FIG. 11)
1. Actuator motor is OFF
2. Ribbon clutch is ON
3. Damper is OFF
4. Leaf spring ankle section 660 is releasing energy Swing Phase (FIG. 12)
1. Actuator motor is ON (changing foot orientation)
2. Ribbon clutch is OFF
3. Damper is OFF
4. Foot leaf spring is slack The maximum dorsiflexion ankle torque during level-ground walking is in the range from 1.5 Ng to 2 Nm/kg, i.e. around 150 Nm for a 100 kg person {2}. With current technology, a variable-damper that can provide such high damping torque and additionally very low damping levels is difficult to build at a reasonable weight and size. Fortunately, the maximum controlled plantar flexion torque is small, typically in the range of 0.3 Nm/kg to 0.4 Ng. Because of these factors, a ribbon stop that engages at a small dorsiflexion angle such as 5 degrees would lower the peak torque requirements of the variable-damper since the peak controlled plantar flexion torque is considerably smaller than the peak dorsiflexion torque.

During stair descent/downhill walking, the human ankle behaves like a damper from foot strike to 90° of dorsiflexion {11}. Beyond that, the ankle behaves like a non-linear spring, storing elastic energy during controlled dorsiflexion. Taking advantage of the biomechanics of the human ankle, it is reasonable to add a passive clutch for resisting dorsiflexion movements beyond 90°, thus allowing for a smaller sized variable damper. A ribbon stop is preferred as a unidirectional clutch because it is lightweight with considerable strength in tension.

Stair Ascent

Figure 13:
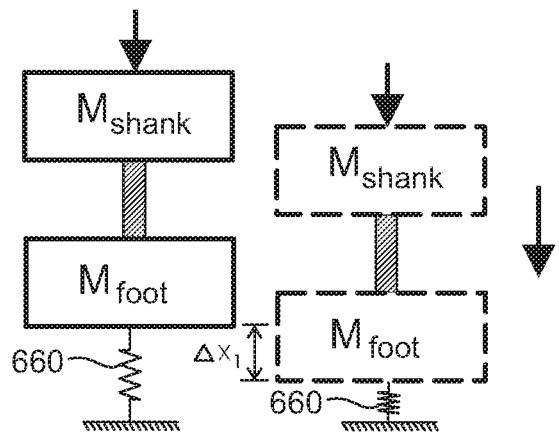
FIGS. 13-15 show the control sequence for embodiment 1 during stair ascent.
Figure 13:
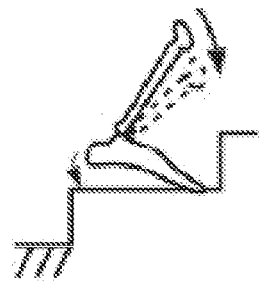
Figure 14:
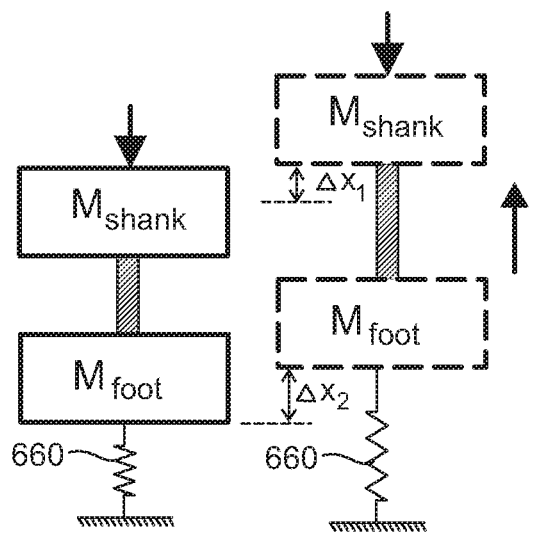
Figure 14:
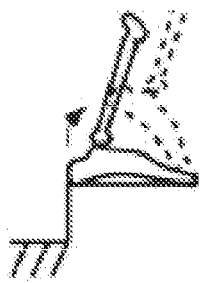
Figure 15:
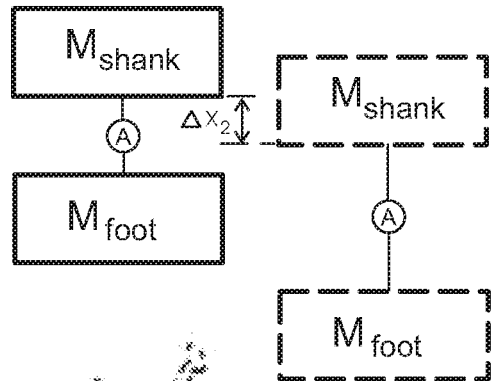
Figure 15:
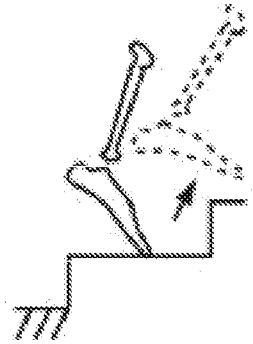

FIGS. 13-15 depict the control sequence of embodiment 1 for stair ascent. It is noted here that there are only three control phases/modes for stair ascent, although the gait cycle for stair ascent can be divided into 5 sub-phases, including Controlled Dorsiflexion 1 (CD1), Powered Plantarflexion 1 (PP1), Controlled Dorsiflexion 2 (CD2), Powered Plantarflexion 1 (PP1), and Swing Phase. The main reason is that in terms of control, we can combine phases PP1, CD2, and PP2 into one single phase since all three phases may be described using the same control law. For ascending a stair, the clutch is engaged and the leaf spring is compressed throughout ground contact (FIG. 13) because the toe strikes the ground first, engaging the ribbon stop during CD ($\Delta X_1 \leq 0$, $\Delta X_2 = 0$). After the heel strikes the ground and then lifts off the ground, the toe leaf spring begins releasing its energy, supplying forward propulsion to the body (FIG. 14). The variable damper may be activated to control the process of energy release from the leaf spring, but in general, the damper is turned off so that all the stored elastic energy is used to propel the body upwards and forwards ($\Delta X_1 \geq 0$, $\Delta X_2 \geq 0$). After toe-off, the actuator controls the equilibrium position of the ankle in preparation for the next step (FIG. 15).

Figure 16:
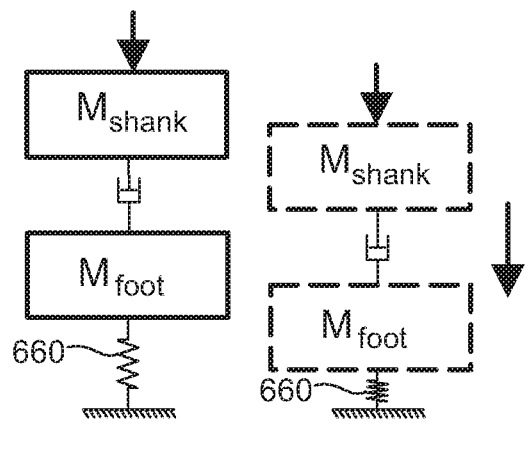
FIGS. 16-19 show the control sequence for embodiment 1 during stair descent.
Figure 16:
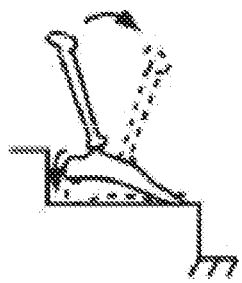
Figure 17:
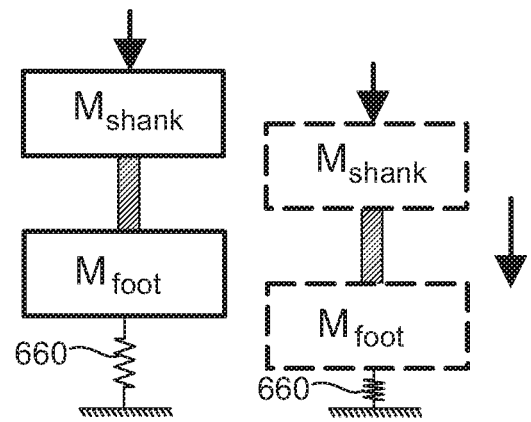
Figure 17:
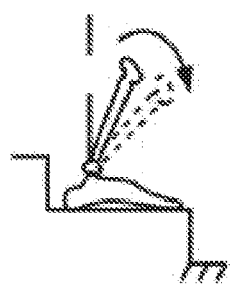
Figure 18:
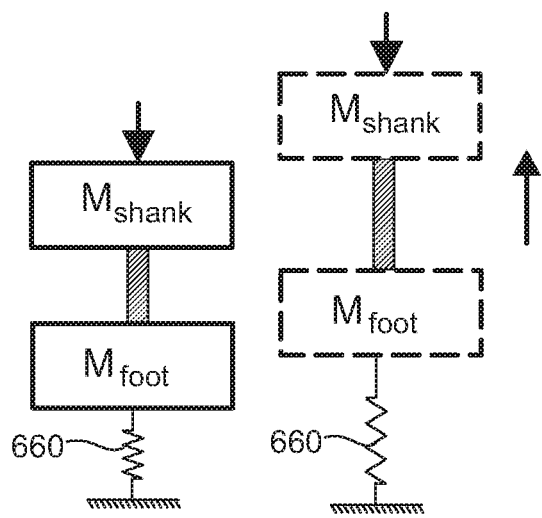
Figure 18:
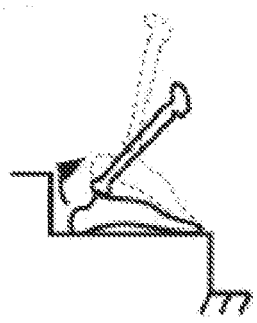
Figure 19:
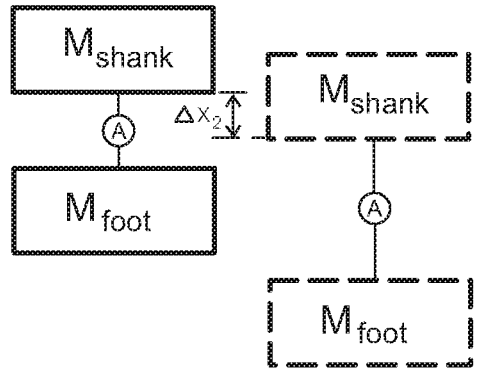
Figure 19:
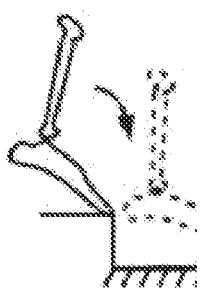
Figure 20:
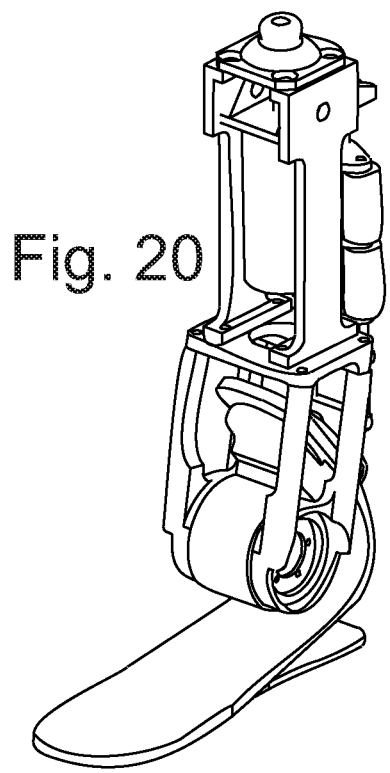
FIG. 20 shows the mechanical design of an anterior view of embodiment 2.
Figure 21:
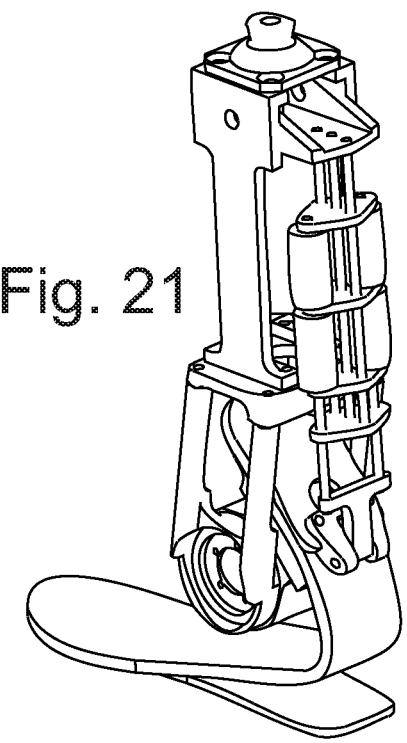
FIG. 21 shows a posterior view of embodiment 2.

The state of each element of the ankle-foot system during these three phases of a stair ascent are listed below:

Controlled Dorsiflexion (FIG. 13)
1. Actuator motor is OFF
2. Ribbon clutch is ON
3. Damper is OFF
4. Leaf spring toe section 660 is being compressed Powered Plantar Flexion (FIG. 14)
1. Actuator motor is OFF
2. Ribbon clutch is ON
3. Damper is OFF
4. Leaf spring toe section 660 is releasing energy Swing Phase (FIG. 15)
1. Actuator motor is ON (changing foot orientation)
2. Ribbon clutch is OFF
3. Damper is OFF
4. Foot leaf spring is slack Stair Descent The control sequence for embodiment 1 for stair descent is depicted in FIGS. 16-19. After forefoot contact, the body has to be lowered until the heel makes contact with the stair tread {11} (FIG. 16). Therefore, the variable damper is activated as energy is dissipated during controlled dorsiflexion ($\Delta X_1 <= 0$, $\Delta X_2 <= 0$). As is shown in FIG. 17, when the foot becomes flat on the ground, the ribbon stop becomes taut, compressing the toe leaf spring ($\Delta X_1 <= 0$, $\Delta X_2 = 0$). During PP, the toe leaf spring releases its energy, propelling the body upwards and forwards (FIG. 18).

The state of each element of the ankle-foot system during the four phases of stair descent are listed below:

Controlled Dorsiflexion 1 (FIG. 16)
1. Actuator motor is OFF
2. Ribbon clutch is OFF
3. Damper is ON
4. Leaf spring toe section 660 is being compressed Controlled Dorsiflexion 2 (FIG. 17)
1. Actuator motor is OFF
2. Ribbon clutch is ON
3. Damper is OFF
4. Leaf spring toe section 660 is being compressed Powered Plantar Flexion (FIG. 18)
1. Actuator motor is OFF
2. Ribbon clutch is ON
3. Damper is OFF
4. Leaf spring toe section 660 is releasing energy Swing Phase (FIG. 19)
1. Actuator motor is ON (changing foot orientation)
2. Ribbon clutch is OFF
3. Damper is OFF
4. Foot leaf spring is slack Sensing for Embodiment 1

The ankle foot system preferably employs an inertial navigation system (INS) for the control of an active artificial ankle joint to achieve a more natural gait and improved comfort over the range of human walking and climbing activities.

To achieve these advantages, an artificial ankle joint must be controlled to behave like a normal human ankle. For instance, during normal level ground walking, the heel strikes the ground first; but when descending stairs, it is the toe which first touches the ground. Walking up or down an incline, either the toe or the heel may strike the ground first, depending upon the steepness of the incline.

A difficult aspect of the artificial ankle control problem is that the ankle joint angle must be established before the foot reaches the ground, so that the heel or toe will strike first, as appropriate to the activity. Reliable determination of which activity is underway while the foot is still in the air presents implacable difficulties for sensor systems presently employed on lower leg artificial devices.

The present invention addresses this difficulty by attaching an inertial navigation system below the knee joint, either on the lower leg segment or on the artificial foot. This system is then used to determine the foot's change in elevation since it last left the ground. This change in elevation may be used to discriminate between level ground walking and descending stairs or steep inclines. The ankle joint angle may then be controlled during the foot's aerial phase to provide heel strike for level ground walking or toe strike upon detection of negative elevation, as would be encountered descending stairs or walking down a steep incline.

Inertial navigation systems rely upon accelerometers and gyroscopes jointly attached to a rigid assembly to detect the assembly's motion and change of orientation. In accordance with the laws of mechanics, these changes may be integrated to measure changes of the system's position and orientation, relative to its initial position and orientation. In practice, however, it is found that errors of the accelerometers and gyros produce ever-increasing errors in the system's estimated position. Inertial navigation systems can address this problem in one of two ways: by the use of expensive, high precision accelerometers and gyroscopes, and by incorporating other, external sources of information about position and orientation, for instance GPS, to augment the purely inertial information. But using either of these alternatives would make the resulting system unattractive for an artificial ankle device.

However, we have found that an unaugmented, purely inertial system based on available low cost accelerometers and rate gyros can provide sufficiently accurate trajectory information to support proper control of the angle of an actuated artificial ankle system.

An Illustrative Control Algorithm

Control of an actuated artificial ankle joint may be implemented as follows:

A. During the foot flat (controlled dorsiflexion) phase of the walking cycle, reset and maintain the measured elevation to zero. When the foot is flat on the ground, its velocity and acceleration are zero. Thus, this particular foot posture serves as a reset point for the integration of angular and linear velocities in the estimation of absolute positions.

B. During the push off phase, when powered plantarflexion begins, measure the upward and downward movements to determine the current elevation relative to the initial zero elevation during the flat foot phase;

C. As long as the elevation remains above zero, maintain the foot orientation that will provide heelstrike; and D. If the elevation decreases below zero, reorient the angle ankle to provide toe-first contact.

The foot flat phase may be detected by the absence of non-centrifugal, non-gravitational, linear acceleration along the length axis of the lower leg. Push off phase may be detected by the upward acceleration along the axis of the lower leg. Elevation>0 and elevation<0 phases are recognized from the change in relative elevation computed by the INS since the end of foot flat phase.

Embodiment 2

Mechanical Design

Figure 22:
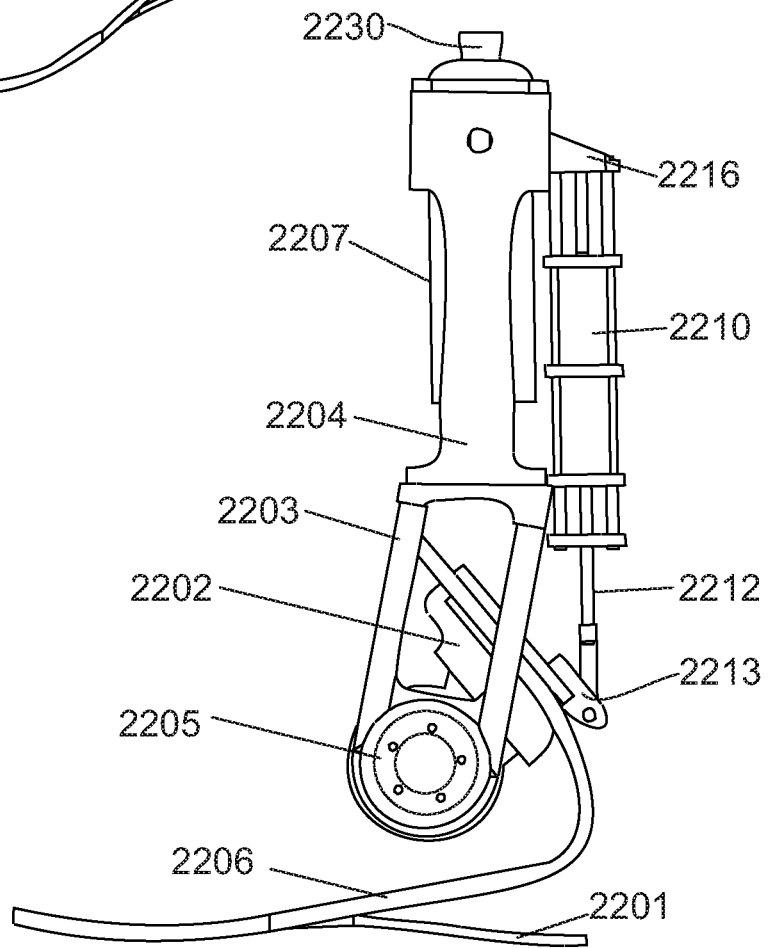
FIG. 22 shows a side elevational view of embodiment 2.

The mechanical design of Embodiment 2 is shown in FIGS. 20-23. As seen in FIG. 22, the foot and ankle system includes an elastic leaf spring structure that provides a heel spring as seen at 2201 and a toe spring as seen at 2206, the elastic leaf spring structure attaches to a brake mount member 2202 that rotates with respect to an ankle joint shank frame 2203 and a tibial side bracket 2204 about a pivot axis at the center of the MR brake seen at 2205. The actuator motor 2207 is mounted within the tibial side bracket 2204 and its drive shaft is coupled through a drive gear (not shown) to rotate the elastic leaf spring structure 2201 and 2206 with respect to the shank frame 2203 and side bracket 2204 about the ankle joint. A catapult mechanism to provide powered plantar flexion during late stance is employed that consists of a series elastic spring element seen at 2210 having an internal slider 2212 that attaches to the brake mount 2202 at the lower actuator mount 2213, and the spring element 2210 attaches to the upper actuator mount 2216 at the top of the tibial side bracket 2204. A standard pyramid mount 2230 at the top of the tibial side bracket 2294 provides a connection to the shin member (not shown).

Figure 23:
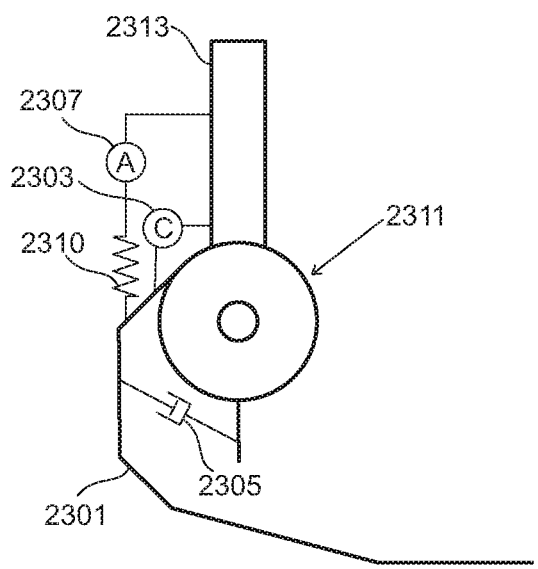
FIG. 23 is a schematic depiction of embodiment 2.

The corresponding schematic of Embodiment 2 is seen in FIG. 23 and is similar to that of Embodiment 1, including the heel and toe leaf spring 2301, variable damper 2305, and ribbon stop 2303. The series elastic spring element is seen at 2310 connected in series with the actuator motor 2307 to form the catapult.

One of the main challenges in the design of an artificial ankle is to have a relatively low-mass actuation system that can provide a large instantaneous output power upwards of 200 Watts during Powered Plantar Flexion (PP) {2,11} Fortunately, the duration of PP is only 15% of the entire gait cycle, and the average power output of the human ankle during the stance phase is much lower than the instantaneous output power during PP. Hence, a catapult mechanism is a compelling solution to this problem.

The catapult mechanism is mainly composed of three components: an actuator motor, a variable damper and/or clutch and an energy storage element. The actuator can be any type of motor system, including electric, shape memory alloy, hydraulic or pneumatic devices, and the series energy storage element can be any elastic element capable of storing elastic energy when compressed or stretched. The damper can be any type of device including hydraulic, magnetorheological, pneumatic, or electrorheological.

With the parallel damper seen at 2305 in FIG. 23 activated to a high damping level or with the parallel clutch 2303 activated, the series elastic spring element 2310 can be compressed or stretched by the actuator 2307 in series to the spring 2310 without the joint rotating. The spring 2310 will provide a large amount of instantaneous output power once the parallel damping device 2305 or clutch 2303 is deactivated, allowing the elastic element 2310 to release its energy. If the actuator 2307 has a relatively long period of time to compress or stretch the elastic element 2310, its mass can be kept relatively low, decreasing the overall weight of the artificial ankle device. In Embodiment 2, the catapult system comprises a magnetorheological variable damper 2305 placed in parallel to the series elastic electric motor system.

Control System

Figure 24:
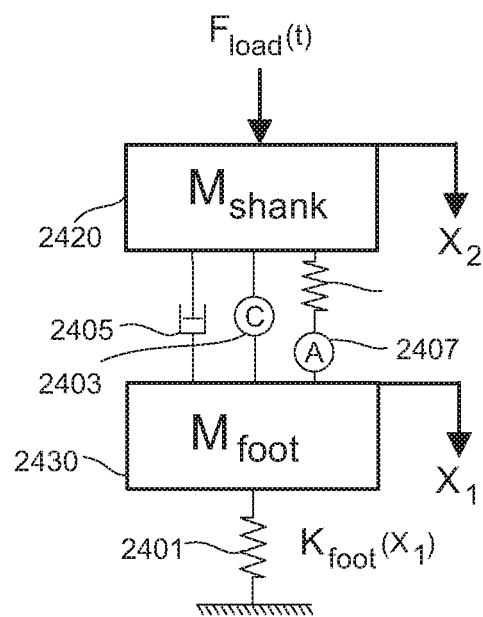
FIG. 24 depicts a lumped parameter model of embodiment 2.

The lumped parameter model of Embodiment 2 is shown in FIG. 24. It is basically the same as the model of Embodiment 1 as depicted in FIG. 8, except that we now place a spring element 2410 in series with the actuator 2407 and the foot mass structure 2430. The main idea here is that if the variable MR damper seen at 2405 outputs high damping, locking the ankle joint, the foot and the shank become one single component. Once the joint is locked, the actuator 2407 compresses or stretches the spring element 2310. Once joint damping is minimized, the spring element 2410 will then push against the shank 2420 to provide forward propulsion during powered plantar flexion.

The control sequence of Embodiment 2 for level-ground walking will be discussed in the next section. Stair ascent/descent can be deduced from the earlier descriptions for embodiment 1, and thus, will not be described herein.

Level-Ground Walking

Figure 25:
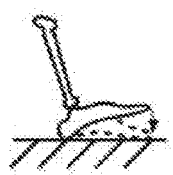
FIGS. 25-28 show the control sequence for embodiment 2 during ground level walking.
Figure 26:
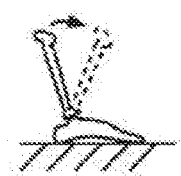
Figure 27:
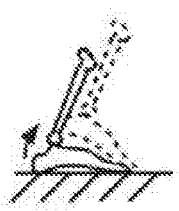
Figure 28:
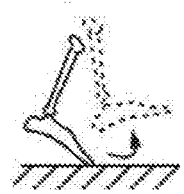

The control sequence of Embodiment 2 for level-ground walking is depicted in FIGS. 25-28. During CP, the actuator controls the stiffness of the ankle by controlling the displacement of the series spring (FIG. 25). During CD, the toe carbon fiber leaf spring 2206 is compressed due to the loading of body weight, while the actuator compresses the series spring to store additional elastic energy in the system (FIG. 26). In this control scheme, inertia and body weight hold the joint in a dorsiflexed posture, enabling the motor to elongate the series spring. In a second control approach, where body weight and inertia are insufficient to lock the joint, the MR variable damper would output a high damping value to essentially lock the ankle joint while the motor stores elastic energy in the series spring. Independent of the catapult control approach, during PP as seen in FIG. 27, as the load from body weight decreases, both the leaf spring and the series catapult spring begin releasing stored elastic energy, supplying high ankle output powers. After toe-off, the actuator controls the position of the foot while both the series spring and the leaf springs are slack as depicted in FIG. 28.

The state of each element of Embodiment 2 of the ankle foot system during the four phases of a level ground walking cycle are listed below:

Controlled Plantar Flexion (FIG. 25)
1. Actuator motor is ON
2. Ribbon clutch is OFF
3. Damper is OFF
4. Leaf spring heel portion at 2201 is being compressed Controlled Dorsiflexion (FIG. 26)
1. Actuator motor is ON
2. Ribbon clutch is ON
3. Damper is OFF
4. Leaf spring toe section 2206 is being compressed Powered Plantar Flexion (FIG. 27)
1. Actuator motor is ON
2. Ribbon clutch is OFF
3. Damper is OFF
4. Leaf spring toe section 2206 is releasing energy Swing Phase (FIG. 28)
1. Actuator motor is ON (changing foot orientation)
2. Ribbon clutch is OFF
3. Damper is OFF
4. Foot leaf spring structure is slack Sensing for Embodiment 2

As with Embodiment 1, an inertial navigation system for the control of the active artificial ankle joint will be employed to achieve a more natural gait and improved comfort over the range of human walking and climbing activities. The manner in which these navigation sensors will be used is similar to that described for Embodiment 1.

Sensing and Control

Figure 29:
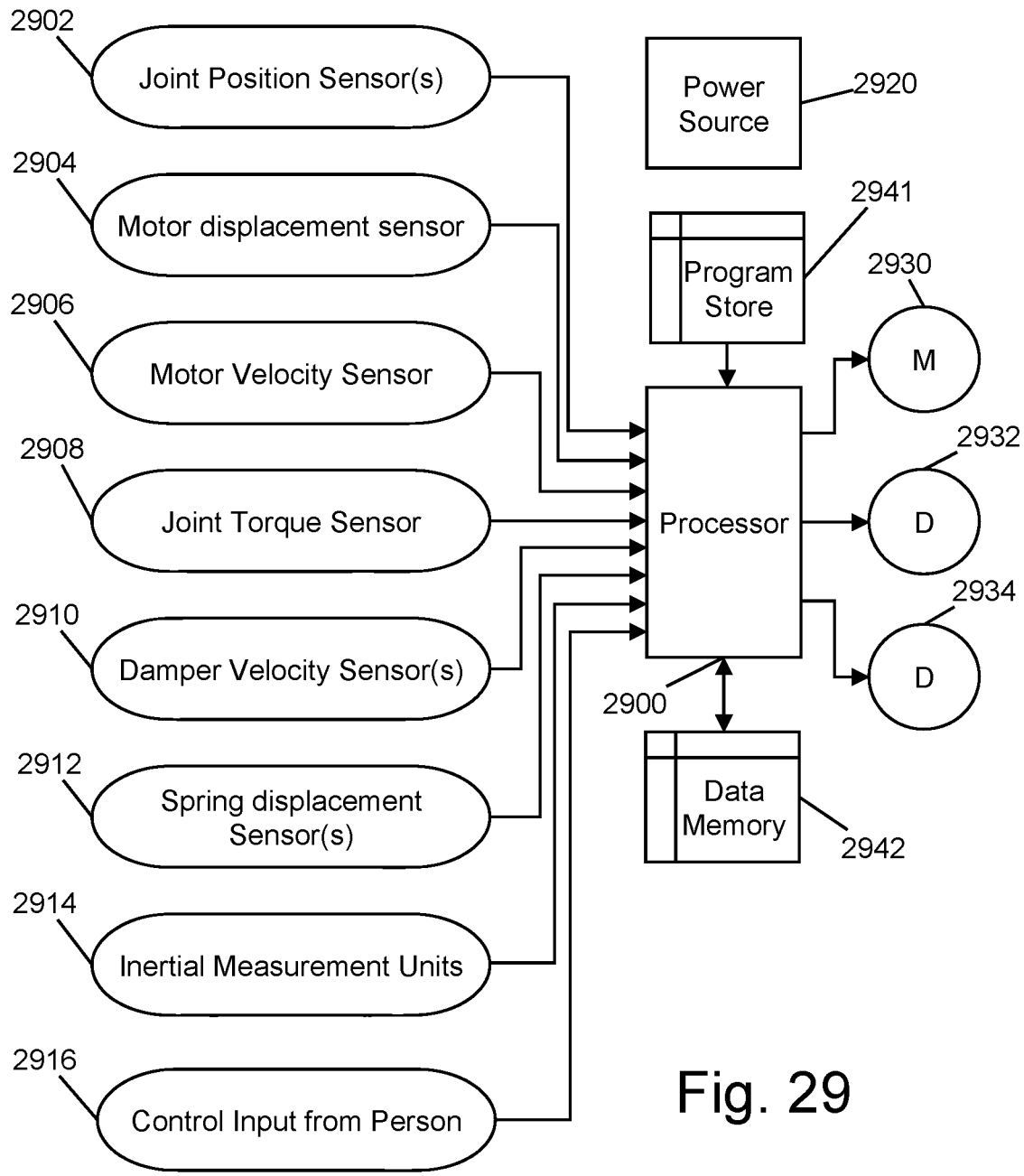
FIG. 29 is a schematic block diagram of a sensing and control mechanism used to control the operation of the motors and dampers in ankle foot systems embodying the invention.

As described above, investigations of the biomechanics of human limbs have revealed the functions performed by the ankle during normal walking over level ground, and when ascending or descending a slope or stairs. As discussed above, these functions may be performed in an artificial ankle joint using motors to act as torque actuators and to position the foot relative to the shin member during a specific times of walking cycle, using springs in combination with controllable dampers to act as linear springs and provide controllable damping at other times in the walking cycle. The timing of these different functions occurs during the walking cycle at times described in detail above. The specific mechanical structures, that is the combinations of motors, springs and controllable dampers used in these embodiments are specifically adapted to perform the functions needed, a variety of techniques may be employed to automatically control the motor and controllable dampers at the times needed to perform the functions illustrated, and any suitable control mechanism may be employed. FIG. 29 depicts the general form of a typical control mechanism in which a multiple sensors are employed to determine the dynamic status of the skeletal structure and the components of the hybrid actuator and deliver data indicative of that status to a processor seen at 2900 which produces control outputs to operate the motor actuator and to control the variable dampers.

The sensors used to enable general actuator operation and control can include:

(1) Position sensors seen at 2902 in FIG. 29 located at the ankle joint axis to measure joint angle (a rotary potentiometer), and at the motor rotor to measure total displacement of the motor's drive shaft (as indicated at 2904) and additionally the motor's velocity (as indicated at 2906). A single shaft encoder may be employed to sense instantaneous position, from which motor displacement and velocity may be calculated by the processor 2900.

(2) A force sensor (strain gauges) to measure the actual torque borne by the joint as indicated at 2908.

(3) Velocity sensors on each of the dampers (rotary encoders) as indicated at 2910 in order to get a true reading of damper velocity.

(4) A displacement sensor on each spring (motor series spring and global damper spring) as indicated at 2912 in order to measure the amount of energy stored.

(5) One or more Inertial Measurement Units (IMUs) seen at 2914 which can take the form of accelerometers positioned on skeletal members from which the processor 2900 can compute absolute orientations and displacements of the artificial joint system. For example, the IMU may sense the relative vertical movement of the foot member relative to its foot flat position during the walking cycle to control foot orientation as discussed above.

(6) One or more control inputs manipulatable by a person, such a wearer of a prosthetic joint or the operator of a robotic system, to control such things as walking speed, terrain changes, etc.

The processor 2900 preferably comprises a microprocessor which is carried on the ankle-foot system and typically operated from the same battery power source 2920 used to power the motor 2930 and the controllable dampers 2932 and 2934. A non-volatile program memory 2941 stores the executable programs that control the processing of the data from the sensors and input controls to produce the timed control signals which govern the operation of the actuator motor and the dampers. An additional data memory seen at 2942 may be used to supplement the available random access memory in the microprocessor 2900.

Instead of directly measuring the deflection of the motor series springs as noted at (4) above, sensory information from the position sensors (1) can be employed. By subtracting the ankle joint angle from the motor output shaft angle, it is possible to calculate the amount of energy stored in the motor series spring. Also, the motor series spring displacement sensor can be used to measure the torque borne by the joint because joint torque can be calculated from the motor series output force.

Many variations exist in the particular sensing methodologies employed in the measurement of the listed parameters. Although this specification describes preferred sensing methods, each has the goal of determining the energy state of the spring elements, the velocities of interior points, and the absolute movement pattern of the ankle joint itself.

REFERENCES

The following published materials provide background information relating to the invention. Individual items are cited above by using the reference numerals which appear below and in the citations in curly brackets.

{1} Palmer, Michael. Sagittal Plane Characterization of Normal Human Ankle Function across a Range of Walking Gait Speeds. Massachusetts Institute of Technology Master's Thesis, 2002.

{2} Gates Deanna H., Characterizing ankle function during stair ascent, descent, and level walking for ankle prosthesis and orthosis design. Master's thesis, Boston University, 2004.

{3} Hansen, A., Childress, D. Miff, S. Gard, S. and Mesplay, K., The human ankle during walking: implication for the design of biomimetric ankle prosthesis, Journal of Biomechanics (In Press).

{4} Koganezawa, K. and Kato, I., Control aspects of artifical leg, IFAC Control Aspects of Biomedical Engineering, 1987, pp. 71-85.

{5} Herr H, Wilkenfeld A. User-Adaptive Control of a Magnetorheological Prosthetic Knee. Industrial Robot: An International Journal 2003; 30: 42-55.

{6} Seymour Ron, Prosthetics and Orthotics: Lower limb and Spinal, Lippincott Williams & Wilkins, 2002.

{7} G. A. Pratt and M. M. Williamson, "Series Elastic Actuators," presented at 1995 IEEE/RSJ International Conference on Intelligent Robots and Systems, Pittsburgh, Pa., {8} Inman V T, Ralston H J, Todd F. Human walking. Baltimore: Williams and Wilkins; 1981.

{9} Hof. A. L. Geelen B. A., and Berg, Jw. Van den, "Calf muscle moment, work and efficiency in level walking; role of series elasticity," Journal of Biomechanics, Vol 16, No. 7, pp. 523-537, 1983.

{10} Gregoire, L., and et al, Role of mono- and bi-articular muscles in explosive movements, International Journal of Sports Medicine 5, 614-630.
{11} Koganezawa, K. and Kato, I., Control aspects of artifical leg, IFAC Control Aspects of Biomedical Engineering, 1987, pp. 71-85.
{12} U.S. Pat. No. 6,517,503 issued Feb. 11, 2003.

CONCLUSION

It is to be understood that the methods and apparatus which have been described above are merely illustrative applications of the principles of the invention. Numerous modifications may be made by those skilled in the art without departing from the true spirit and scope of the invention.

What is claimed is:

1. A prosthetic, orthotic or exoskeletal ankle joint device comprising:
    a) a motor adapted to exert a torque about an ankle joint;
    b) a spring operatively coupled to the motor;
    c) an artificial sensory system comprising at least one gyroscope, and at least one accelerometer; and
    d) a processor linking the motor and the sensory system, wherein the processor computes, based on signals from the at least one gyroscope and the at least one accelerometer, an elevation of the device relative to an absolute position of a point at the ankle joint device, wherein the processor outputs a control sequence for stair descent in which during a swing phase an angle of the ankle joint is reoriented for toe-first contact upon detection of an elevation below zero relative to an initial position of the point at the ankle joint, and wherein the processor causes, subsequent to toe-first contact and during a stance phase of stair descent, a damping response to be applied to the ankle joint to thereby control ankle dorsiflexion movement.

2. The device of claim 1, wherein the artificial sensory system further includes a velocity sensor.

3. The device of claim 1, wherein the artificial sensory system further includes a position sensor that includes at least one sensor selected from the group consisting of a joint angular position sensor, motor shaft angular position sensor and an inertial absolute orientation position sensor.

* * * * *